(12) United States Patent
Koo

(10) Patent No.: US 11,994,510 B2
(45) Date of Patent: May 28, 2024

(54) DIAGNOSIS AND TREATMENT OF FUSARIOSIS AND SCEDOSPORIOSIS

(71) Applicant: The Brigham and Women's Hospital, Inc., Boston, MA (US)

(72) Inventor: Sophia Koo, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 1168 days.

(21) Appl. No.: 16/341,265

(22) PCT Filed: Oct. 11, 2017

(86) PCT No.: PCT/US2017/056107
§ 371 (c)(1),
(2) Date: Apr. 11, 2019

(87) PCT Pub. No.: WO2018/071519
PCT Pub. Date: Apr. 19, 2018

(65) Prior Publication Data
US 2020/0041484 A1 Feb. 6, 2020

Related U.S. Application Data

(60) Provisional application No. 62/406,441, filed on Oct. 11, 2016.

(51) Int. Cl.
*G01N 33/497* (2006.01)
*C12Q 1/04* (2006.01)

(52) U.S. Cl.
CPC ............. *G01N 33/497* (2013.01); *C12Q 1/04* (2013.01); *G01N 2033/4977* (2013.01)

(58) Field of Classification Search
None
See application file for complete search history.

(56) References Cited

U.S. PATENT DOCUMENTS

| 6,221,026 | B1* | 4/2001 | Phillips | G01N 33/497 600/529 |
|---|---|---|---|---|
| 6,503,713 | B1 | 1/2003 | Rana | |
| 7,605,367 | B2 | 10/2009 | Miller et al. | |
| 10,031,125 | B2* | 7/2018 | Koo | C12Q 1/025 |
| 10,960,002 | B2* | 3/2021 | Koo | C12Q 1/04 |
| 2007/0003996 | A1 | 1/2007 | Hitt et al. | |
| 2009/0078865 | A1 | 3/2009 | Zapata et al. | |
| 2010/0291617 | A1 | 11/2010 | Trevejo et al. | |
| 2013/0168548 | A1 | 7/2013 | Wang et al. | |

FOREIGN PATENT DOCUMENTS

| WO | WO 2014/039856 | 3/2014 |
|---|---|---|
| WO | WO 2015/187938 | 12/2015 |

OTHER PUBLICATIONS

International Search Report and Written Opinion dated Dec. 22, 2017 in international application No. PCT/US2017/056107, 11 pages.
Antachopoulos et al., "Immunotherapy against invasive mold infections," Immunotherapy, Jan. 2012, 4(1):107-120.
Araujo et al., "Mould Infections: A Global Threat to Immunocompromised Patients," Combating Fungal Infections, Springer, 2010, Chapter 1, pp. 1-19.
Cortez et al., "Infections caused by *Scedosporium* spp," Clin Microbial Rev., Jan. 2008, 21(1):157-197.
Czarnik, "Encoding methods for combinatorial chemistry," Curr. Opin. Chem. Bio., May 1997, 1(1):60-66.
Davis et al., "Spore biomarker detection using a MEMS differential mobility spectrometer," 12th International Conference on Transducers, Solid-State Sensors, Actuators and Microsystems, Jun. 2003, 2:1233-1238.
Fong et al., "Automated Peak Detection and Matching Algorithm for Gas Chromatography—Differential Mobility Spectrometry," Anal .Chem., Mar. 2011, 83(5):1537-1546.
Gil-Lamaignere et al., "Amphotericin B lipid complex exerts additive antifungal activity in combination with polymorphonuclear leucocytes against Scedosporium prolificans and Scedosporium apiospermum," J. Antimicrob. Chemother., Dec. 2002, 50( 6):1027-1030.
Gil-Lamaignere et al., "Antifungal triazoles and polymorphonuclear leukocytes synergize to cause increased hyphal damage to Scedosporium prolificans and Scedosporium apiospermum," Antimicrob. Agents Chemother., Jul. 2002, 46(7):2234-2237.
Gil-Lamaignere et al., "Inteferon gamma and granulocyte-macrophage colony-stimulating factor augment the antifungal activity of human polymorphonuclear leukocytes against *Scedosporium* spp.: comparison with *Aspergillus* spp," Med. Mycol., May 2005, 43(3):253-260.
Kanu et al., "Ion mobility spectrometry detection for gas chromatography," J. Chromatogr. A., 2008, 1177(1):12-27.
Kanu et al., "Ion mobility—mass spectrometry," J. Mass Spectrom., Jan. 2008, 43(1):1-22.
Kesson et al., "Scedosporium prolificans osteomyelitis in an immunocompetent child treated with a novel agent, hexadecylphospocholine (miltefosine), in combination with terbinafine and voriconazole: a case report," Infect. Dis., May 2009, 48(9):1257-1261.
Kolakowski et al., "Review of applications of high-field asymmetric waveform ion mobility spectrometry (FAIMS) and differential mobility spectrometry (DMS)," Analyst, 2007, 132(9):842-864.
Krebs et al., "Detection of Biological and Chemical Agents Using Differential Mobility Spectrometry (DMS) Technology," IEEE Sensors Journal, Jul. 2005, 5(4):696-703.
Luong et al., "Gas Chromatography with state-of-the-art micromachined differential mobility detection: Operation and industrial applications." J. Chromatogr. Sci., May 2006, 44(5):276-286.
Miller et al., "A MEMS Radio-Frequency Ion Mobility Spectrometer for Chemical Agent Detection," Sensors and Actuators, Jul. 2001, 91(3):301-312.

(Continued)

*Primary Examiner* — Vera Afremova
(74) *Attorney, Agent, or Firm* — Fish & Richardson P.C.

(57) ABSTRACT

Methods for diagnosing, treating, and monitoring the treatment of fusariosis or scedosporiosis are described. The methods can include detecting the presence of one or more volatile organic compounds (VOCs) in the breath of subjects suspected of having fusariosis or scedosporiosis.

10 Claims, 24 Drawing Sheets

(56) References Cited

OTHER PUBLICATIONS

Milroy et al., "Aspergillosis of the nose and paranasal sinuses." J. Clin. Pathol., Feb. 1989, 42(2):123-127.

Nazarov et al., "Pressure effects in differential mobility spectrometry," Anal. Chem., Nov. 2006, 78(22):7697-7706.

Ortoneda et al., "Liposomal amphotericin B and granulocyte colony-stimulating factor therapy in a murine model of invasive infection by Scedosporium prolificans," J. Antimicrob. Chemother., Mar. 2002, 49(3):525-529.

PCT International Preliminary Report on Patentability in International Appln. No. PCT/US2017/056107, dated Apr. 16, 2019, 7 pages.

Shnayderman et al., "Species-specific bacteria identification using differential mobility spectrometry and bioinformatics pattern recognition." Anal. Chem., Sep. 2005, 77(18):5930-5937.

Steinbach et al., "Scedosporium prolificans osteomyelitis in an immunocompetent child treated with voriconazole and caspofungin, as well as locally applied polyhexamethylene biguanide," J. Clin. Microbiol., Aug. 2003, 41(8):3981-3985.

Walsh et al., "Treatment of aspergillosis: clinical practice guidelines of the Infectious Diseases Society of America," Clinical Infectious Diseases, Feb. 2008, 46(3):327-360.

\* cited by examiner (mainlib) cis-α-Bisabolene (mainlib) Naphthalene, 1,2,3,5,6,7,8,8a-octahydro-1,8a-dimethyl-7-(1-methylethenyl)-, [1R-(1α,7β,8aα)]-

(mainlib) Naphthalene, 1,2,3,5,6,7,8,8a-octahydro-1,8a-dimethyl-7-(1-methylethenyl)-, [1S-(1α, 7α,8aα)]-

(mainlib) (1S,2R,5R)-2-Methyl-5-((R)-6-methylhept-5-en-2-yl)bicyclo[3.1.0]hexan-2-ol (mainlib) Cyclohexene, 6-ethenyl-6-methyl-1-(1-methylethyl)-3-(1-methylethylidene)-, (S)-

(mainlib) Tricyclo[5.4.0.0(2,8)]undec-9-ene, 2,6,6,9-tetramethyl-,(1R,2S,7R,8R)-

(mainlib) 1H-Cyclopropa[a]naphthalene, 1a,2,3,5,6,7,7a,7b-octahydro-1,1,7,7a-tetramethyl-, [1aR-(1aα,7α,7aα,7bα)]-

(mainlib) Azulene, 1,2,3,3a,4,5,6,7-octahydro-1,4-dimethyl-7-(1-methylethenyl)-, [1R-(1α,3aβ,4α,7β)]-

(mainlib) (1S,4aR,7R)-1,4a-Dimethyl-7-(prop-1-en-2-yl)-1,2,3,4,4a,5,6,7-octahydronaphthalene (mainlib) Aromandendrene (mainlib) Alloaromadendrene (mainlib) Naphthalene, 1,2,3,4,4a,5,6,8a-octahydro-4a,8-dimethyl-2-(1-methylethenyl)-, [2R-(2α,4aα,8aβ)]-

(mainlib) Naphthalene, 1,2,3,4,4a,5,6,8a-octahydro-4a,8-dimethyl-2-(1-methylethenyl)-, [2R-(2α,4aα,8aβ)]-

(mainlib) Epizonarene (mainlib) 1H-Indene, 2,3,3a,4-tetrahydro-3,3a,6-trimethyl-1-(1-methylethyl)-

(mainlib) β-Guaiene ial Nos.
DIAGNOSIS AND TREATMENT OF FUSARIOSIS AND SCEDOSPORIOSIS

CLAIM OF PRIORITY

This application is a § 371 National Stage Application of PCT/US2017/056107, filed Oct. 11, 2017, which claims the benefit of U.S. Provisional Patent Application Serial Nos. 62/406,441, filed on Oct. 11, 2016. The entire contents of the foregoing are hereby incorporated by reference.

FEDERALLY SPONSORED RESEARCH OR DEVELOPMENT

This invention was made with Government support under Grant No. K23AI097225 awarded by the National Institutes of Health. The Government has certain rights in the invention.

TECHNICAL FIELD

Provided herein are methods for diagnosing, treating, and monitoring the treatment of subjects with fusariosis and/or scedosporiosis. The methods can include detecting the presence of one or more volatile organic compounds (VOCs) in the breath of subjects suspected of having fusariosis and/or scedosporiosis.

BACKGROUND

*Fusarium, Scedosporium,* and *Lomentospora* species, all of which are molds, cause severe, life-threatening infections in immunocompromised patients. Infections caused by these species have similar clinical manifestations to other invasive mycoses, such as invasive aspergillosis or mucormycosis, although these species frequently have intrinsic resistance to many antifungal drugs. The diagnosis of fusariosis and scedosporiosis (encompassing infections caused by *Scedosporium* and *Lomentospora*) is exceedingly challenging, often requiring a biopsy procedure for definitive diagnosis. Because of the fulminant nature of these infections, their propensity for adventitious sporulation and dissemination throughout the body, and the lack of noninvasive, reliable diagnostics for these infections, mortality associated with these infections remains high, exceeding 50%.

SUMMARY

As described herein, the present inventors have a unique, species-specific profile of volatile organic compounds (VOCs) produced by *Fusarium, Scedosporium,* and *Lomentospora* species, and other pathogenic fungi in vitro that can be used to distinguish pathogenic fungal species from each other. As shown herein, gas chromatography (GC), mass spectrometry (MS), GC-MS, GC-MS/MS, and differential mobility spectrometry (DMS) can be used for the rapid discrimination between fungal species using pattern-based detection of these species-specific VOC profiles. The methods can be used to accurately identify patients with fusariosis and/or scedosporiosis via direct detection of a pattern of VOCs in their breath.

Described herein are methods for diagnosing a subject with fusariosis or scedosporiosis. The methods include obtaining a sample comprising breath of a subject or suspected of comprising *Fusarium* or *Scedosporium* species fungi isolated from a subject; detecting the presence in the sample of one, two, three, or more volatile organic compounds (VOCs) produced by the *Fusarium* or *Scedosporium* species in a sample comprising breath from the subject or headspace from a culture suspected of comprising *Fusarium* or *Scedosporium* isolated from the subject, wherein the VOCs are selected from the group listed in Table 1 (*Scedosporium*) and/or Table 2 (*Fusarium*); and diagnosing a subject as having fusariosis or scedosporiosis when there are one, two, three or more of the VOCs present in the sample.

In some embodiments, the methods include:
(i) detecting the presence in the sample of γ-gurjunene; and diagnosing a subject who has γ-gurjunene in the sample as having scedosporiosis; or
(ii) detecting the presence in the sample of caryophyllene; and diagnosing a subject who has caryophyllene as having fusariosis, In some embodiments, the sample comprises headspace from a culture.

Also provided herein are methods for treating a subject who has an invasive fungal infection. The methods include obtaining a sample comprising breath of a subject or headspace from a culture suspected of comprising *Fusarium* or *Scedosporium* isolated from a subject; detecting the presence in the sample of one, two, three, or more VOCs selected from the group listed in Table 1 (*Scedosporium*) and/or Table 2 (*Fusarium*); and administering an antifungal treatment to a subject who has one, two, three, or more of the VOCs listed in Table 1 (*Scedosporium*) and/or Table 2 (*Fusarium*).

In some embodiments, the treatment comprises administration of one or more doses of one or more antifungal compounds.

In addition, provided herein are methods for detecting the presence of an *Scedosporium apiospermum, S. prolificans,* or *S. boydii* infection in a subject, the method comprising: obtaining a sample comprising breath of a subject, or headspace from a culture suspected of comprising *Scedosporium* isolated from a subject; determining the presence of one, two, three, or more of the VOCs selected from the group consisting of 1H-Indene, 2,3,3a,4-tetrahydro-3,3a,6-trimethyl-1-(1-methylethyl)-, β-guaiene, α-longipinene, β-longipinene, α-gurjunene, β-gurjunene, γ-gurjunene, isocomene, trans-α-bergamotene, himachalene, bisabolene, cadinene, selina-5,11-diene, aromandendrene, alloaromadendrene, naphthalene, 1,2,4a,5,6,8a-hexahydro-4,7-dimethyl-1-(1-methylethyl)-, selinene, and epizonarene in the sample, wherein:

the presence of one, two, three, or more, e.g., all, of camphene, 1H-Indene, 2,3,3a,4-tetrahydro-3,3a,6-trimethyl-1-(1-methylethyl)-, β-guaiene, α-longipinene, β-longipinene, α-gurjunene, β-gurjunene, γ-gurjunene, isocomene, trans-α-bergamotene, himachalene, bisabolene, cadinene, selina-5,11-diene, aromandendrene, alloaromadendrene, naphthalene, 1,2,4a,5,6,8a-hexahydro-4,7-dimethyl-1-(1-methylethyl)-, selinene, and epizonarene indicates the presence of an *S. apiospermum* infection;

the presence of only himachalene and γ-gurjunene indicates the presence of an *S. prolificans* infection; and the presence of only γ-gurjunene indicates the presence of an *S. boydii* infection in the subject.

Further, provided herein are methods for detecting the presence of a *Fusarium oxysporum, F. proliferatum, F. solani,* or *F. verticillioides* infection in a subject. The methods include obtaining a sample comprising breath of a subject, or headspace from a culture suspected of comprising *Fusarium* isolated from a subject; determining the presence of one, two, three, or more of the VOCs selected from the group listed in Table 2 in the sample, wherein:

the presence of one, two, three, or more, e.g., all, of cyclosativene, β-longipinene, 3-isopropyl-6,8a-dimethyl-1,2,4,5,8,8a-hexahydroazulene, isocomene, γ-elemene, trans-α-bergamotene, himachalene, caryophyllene, santalene, bisabolene, valencene, eremophilene, isodaucene, and germacrene B indicates the presence of an *F. oxysporum* infection;

the presence of megastigma-4,6(Z),8(E)-triene, β-longipinene, 3-isopropyl-6,8a-dimethyl-1,2,4,5,8,8a-hexahydroazulene, isocomene, γ-elemene, α-gurjunene, trans-α-bergamotene, caryophyllene, santalene, bisabolene, humulene, cadinene, valencene, eremophilene, isodaucene, sesquisabinene hydrate, and germacrene B indicates the presence of an *F. proliferatum* infection;

the presence of only caryophyllene and humulene indicates the presence of an *F. solani* infection; and the presence of α-gurjunene, α-elemene, trans-α-bergamotene, himachalene, caryophyllene, γ-elemene, santalene, humulene, valencene, and germacrene B indicates the presence of an *F. verticillioides* infection in the subject.

In some embodiments, the methods include selecting, and optionally administering, a therapy comprising an azole, e.g., voriconazole, for a subject who has an *F. proliferatum* or *F. oxysporum* infection; or selecting, and optionally administering, a therapy comprising amphotericin B (AMB), e.g., D-AMB or a lipid formulation of AMB, for a subject who has an *F. solani* or *F. verticilloides* infection.

Additionally provided herein are methods for monitoring efficacy of a treatment for fusariosis or scedosporiosis in a subject. The methods include determining a first level of one, two, three, or more volatile organic compounds (VOCs) produced by the species in a sample comprising breath from the subject or headspace from a culture suspected of comprising *Fusarium* or *Scedosporium* isolated from the subject, wherein the VOCs are selected from the group listed in Table 1 (*Scedosporium*) and/or Table 2 (*Fusarium*), in the subject; administering a treatment for fusariosis or scedosporiosis to the subject; determining a second level of the VOCs in a sample obtained after administration of the treatment to the subject; and comparing the first and second levels of VOCs, wherein a decrease in the VOCs indicates that the treatment has been effective in treating the fusariosis or scedosporiosis in the subject, and an increase or no change indicates that the treatment has not been effective in treating the fusariosis or scedosporiosis in the subject.

In some embodiments, the treatment comprises administration of one or more doses of one or more antifungal compounds.

In addition, provided herein are methods for identifying a candidate compound for the treatment of fusariosis or scedosporiosis. The methods include providing a test culture comprising one or more *Fusarium* or *Scedosporium* species; detecting a baseline level of fungal VOCs in the headspace of the culture in the absence of the test compound, wherein the VOCs are selected from the group listed in Table 1 (*Scedosporium*) and/or Table 2 (*Fusarium*), in the subject; contacting the test culture with a test compound; determining a second level of the VOCs in a the test culture; comparing the second level of VOCs to the baseline level; and identifying a test compound that decreases levels of fungal VOCs in the test culture as a candidate compound for the treatment of fusariosis or scedosporiosis.

In some embodiments of the various methods described herein, the antifungal compound is an amphotericin B formulation or an azole antifungal compound.

In some embodiments of the various methods described herein, determining the presence of a VOC comprises assaying the sample to detect the presence the VOC. In some embodiments, assaying the sample to detect the presence the VOC comprises using a gas chromatography (GC) or spectrometry method. In some embodiments, the spectrophotometry method is mobility spectrometry (IMS) or differential mobility spectrometry (DMS).

In some embodiments of the various methods described herein, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety, including especially U.S. Application Ser. No. 61/698,155, filed on Sep. 7, 2012, and PCT/US2013/058560, filed on Sep. 6, 2013, and published as WO 2014/039856. In case of conflict, the present specification, including definitions, will control.

Other features and advantages of the invention will be apparent from the following detailed description and figures, and from the claims.

DETAILED DESCRIPTION

Figure 1A:
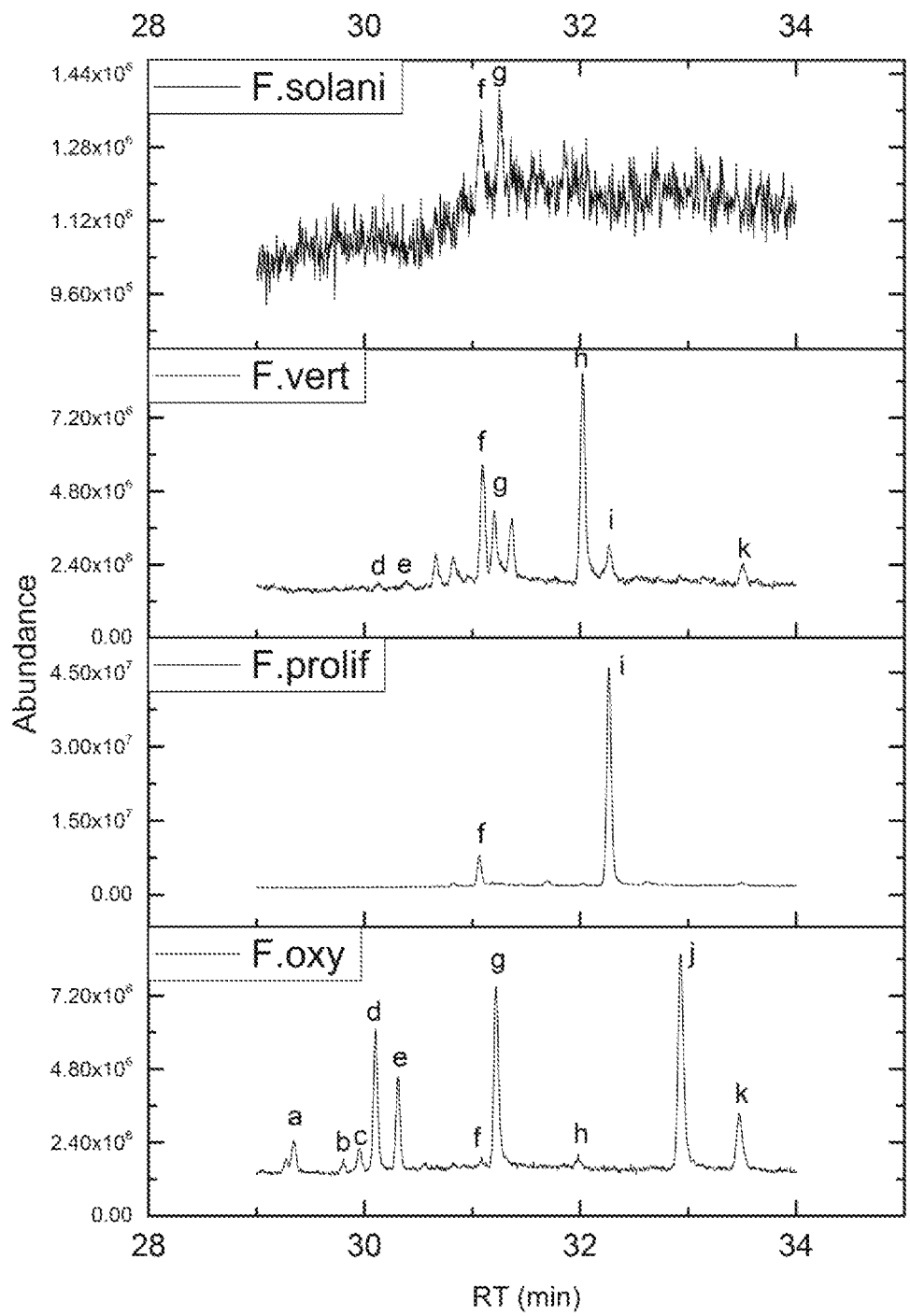
FIG. 1A. Sample GC-MS total ion chromatograms of headspace gas from cultures of *Fusarium solani, Fusarium verticillioides, Fusarium proliferatum,* and *Fusarium oxysporum;* (a) β-longipinene, (b) 3-isopropyl-6,8a-dimethyl-1,2,4,5,8,8a-hexahydroazulene, (c) isocomene, (d) γ-elemene, (e) trans-α-bergamotene, (f) himachalene, (g) caryophyllene, (h)santalene, (i) bisabolene, (j) valencene, (k) germacrene B; full GC-MS fragmentation patterns as outlined below.
Figure 1B:
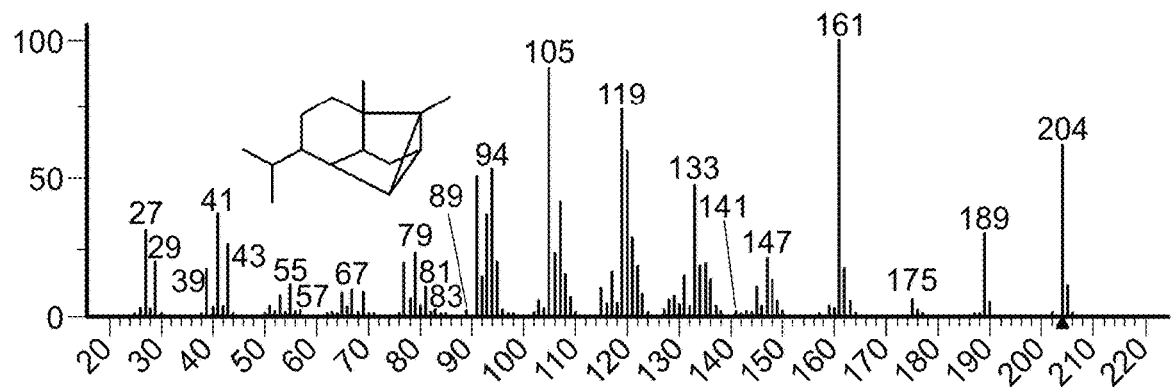
FIG. 1B. MS electron ionization fragmentation pattern for cyclosativene, present in cultures of *Fusarium oxysporum.*
Figure 1C:
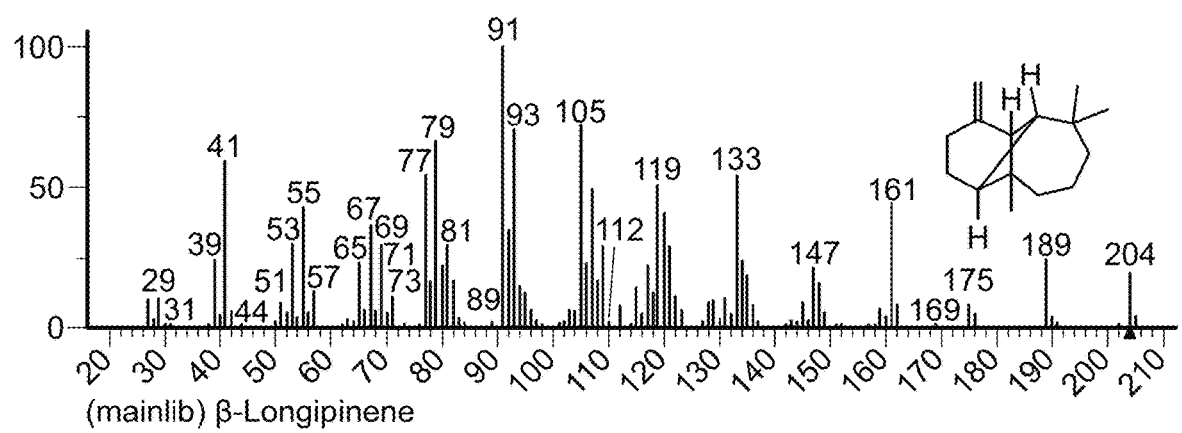
FIG. 1C. MS electron ionization fragmentation pattern for β-longipinene, present in cultures of *Fusarium oxysporum. Fusarium proliferatum, Scedosporium apiospermum,* and in the breath of 2 patients with disseminated *S. apiospermum* infection.
Figure 1D:
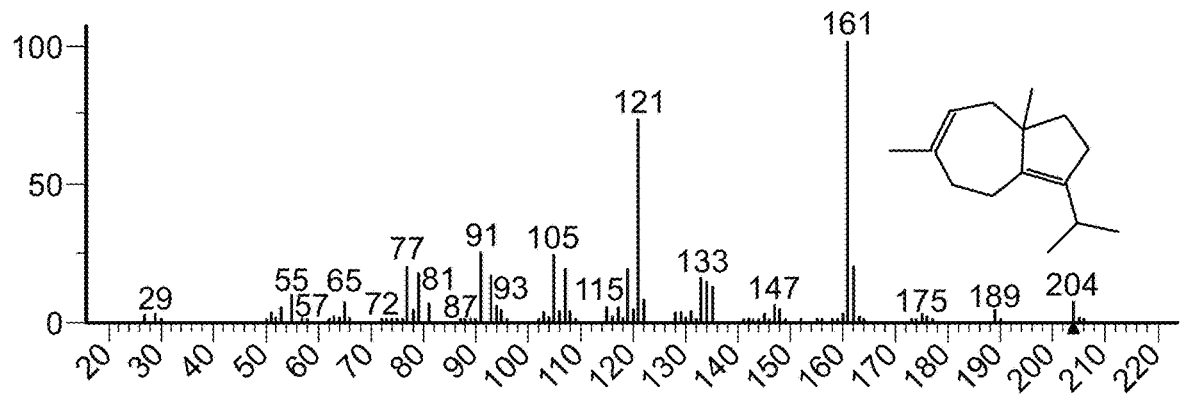
FIG. 1D. MS electron ionization fragmentation pattern for 3-isopropyl-6,8a-dimethyl-1,2,4,5,8,8a-hexahydroazulene, present in cultures of *Fusarium oxysporum. Fusarium proliferatum.*
Figure 1E:
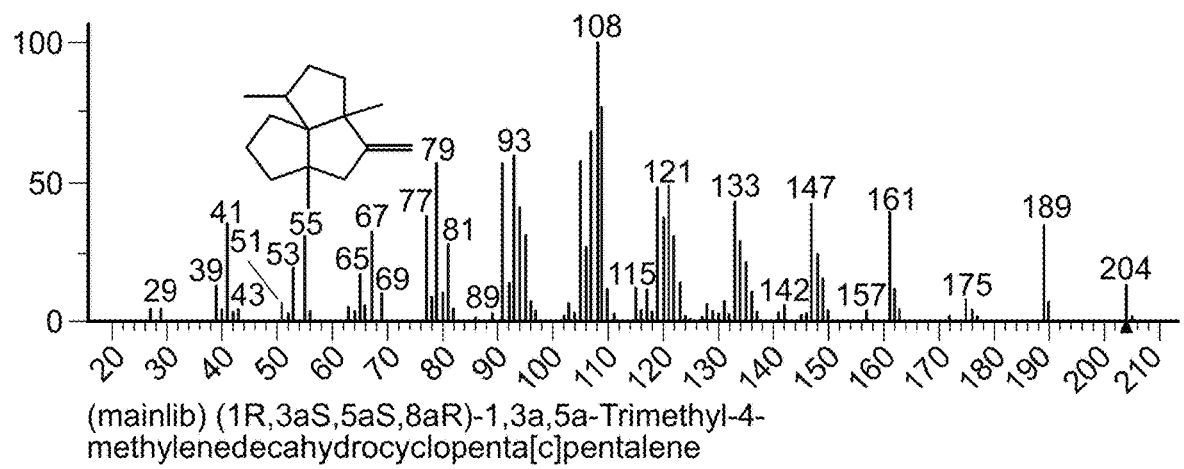
FIG. 1E. MS electron ionization fragmentation pattern for isocomene, present in cultures of *Fusarium oxysporum. Fusarium proliferatum, Scedosporium apiospermum,* and in the breath of 2 patients with disseminated *S. apiospermum* infection.
Figure 1F:
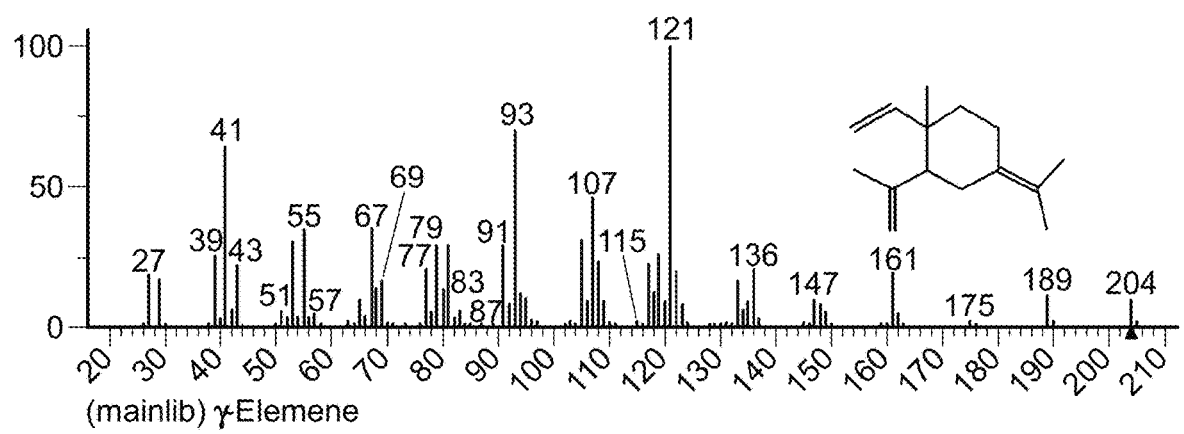
FIG. 1F. MS electron ionization fragmentation pattern for γ-elemene, present in cultures of *Fusarium oxysporum. Fusarium proliferatum, Fusarium verticillioides.*
Figure 1G:
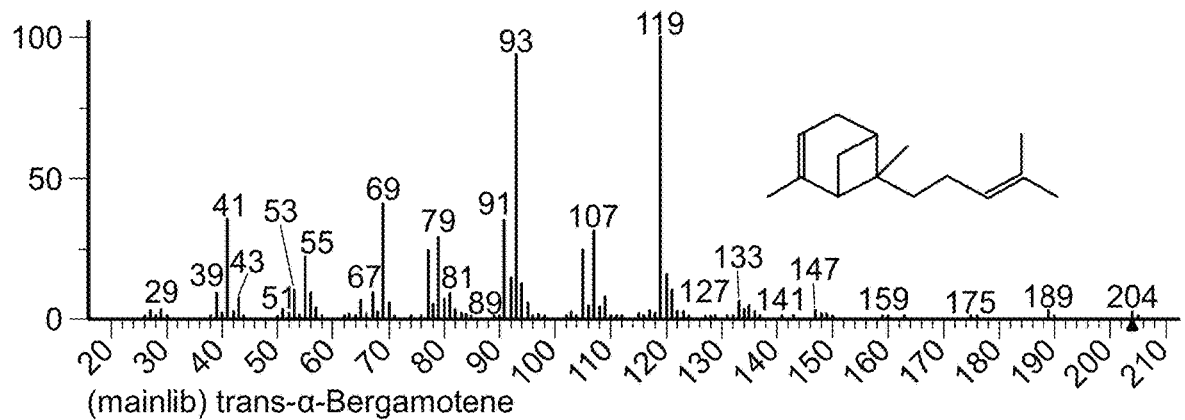
FIG. 1G. MS electron ionization fragmentation pattern for trans-α-bergamotene, present in cultures of *Fusarium oxysporum. Fusarium proliferatum, Fusarium verticillioides, Scedosporium apiospermum.*
Figure 1H:
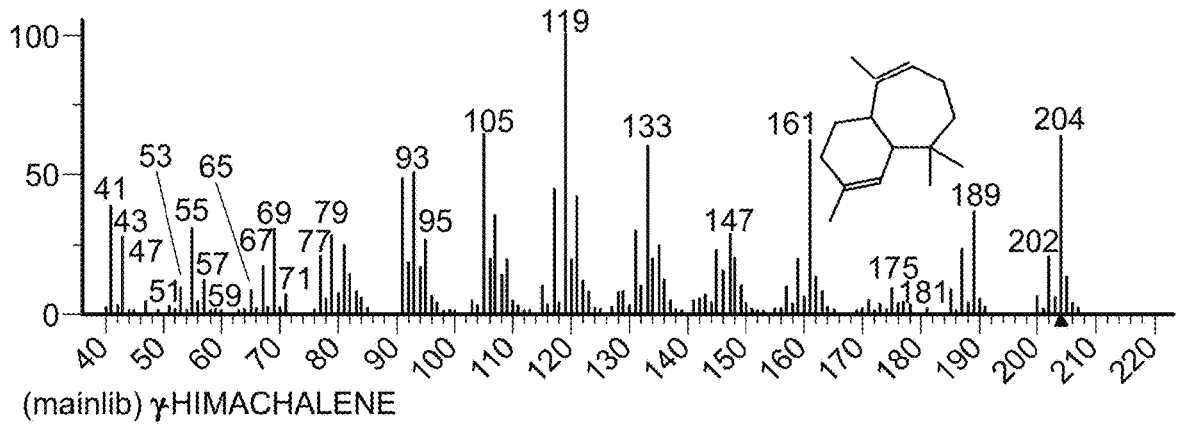
FIG. 1H. MS electron ionization fragmentation pattern for himachalene, present in cultures of *Fusarium oxysporum, Fusarium verticillioides, Scedosporium apiospermum, Lomentospora prolificans.*
Figure 1I:
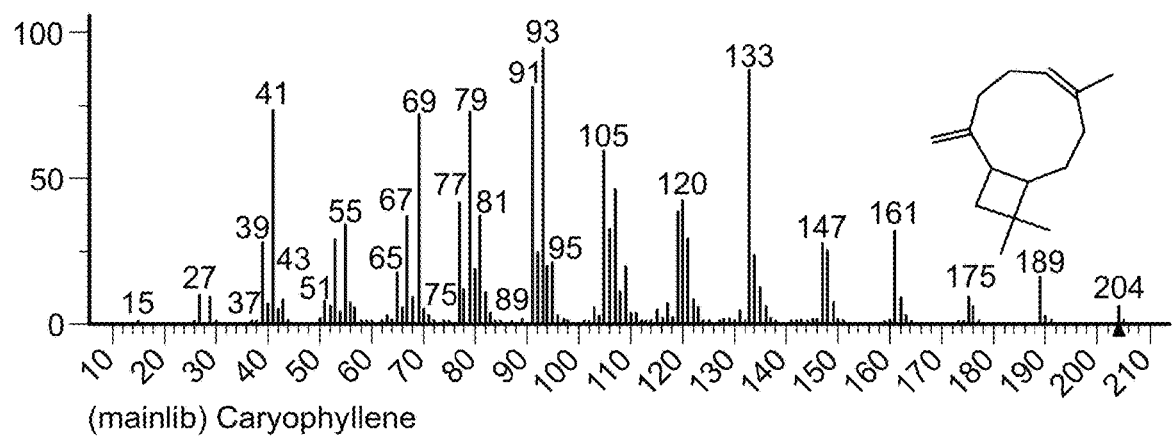
FIG. 1I. MS electron ionization fragmentation pattern for caryophyllene, present in cultures of *Fusarium oxysporum, Fusarium proliferatum, Fusarium solani, Fusarium verticillioides*.
Figure 1J:
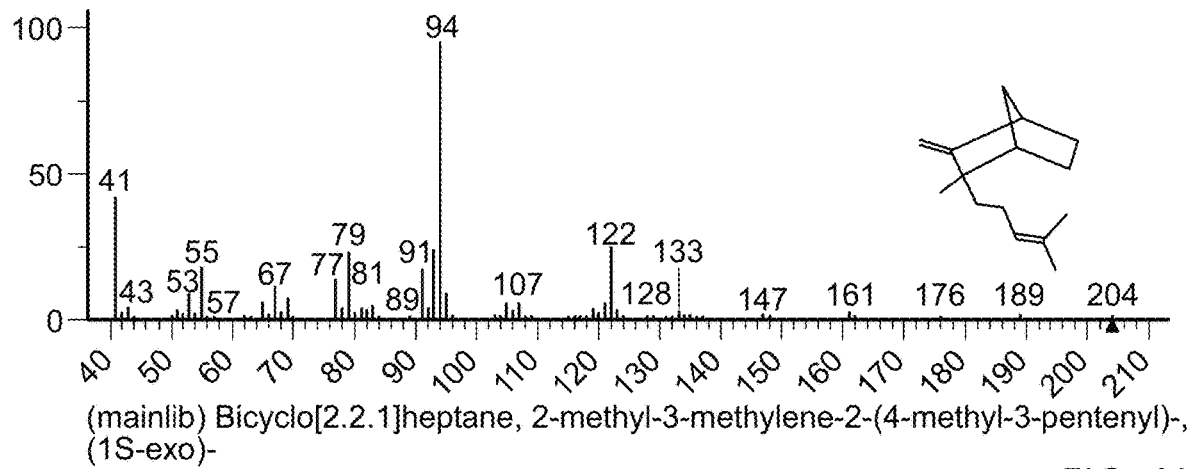
FIG. 1J. MS electron ionization fragmentation pattern for santalene, present in cultures of *Fusarium oxysporum, Fusarium proliferatum, Fusarium verticillioides*.
Figure 1K:
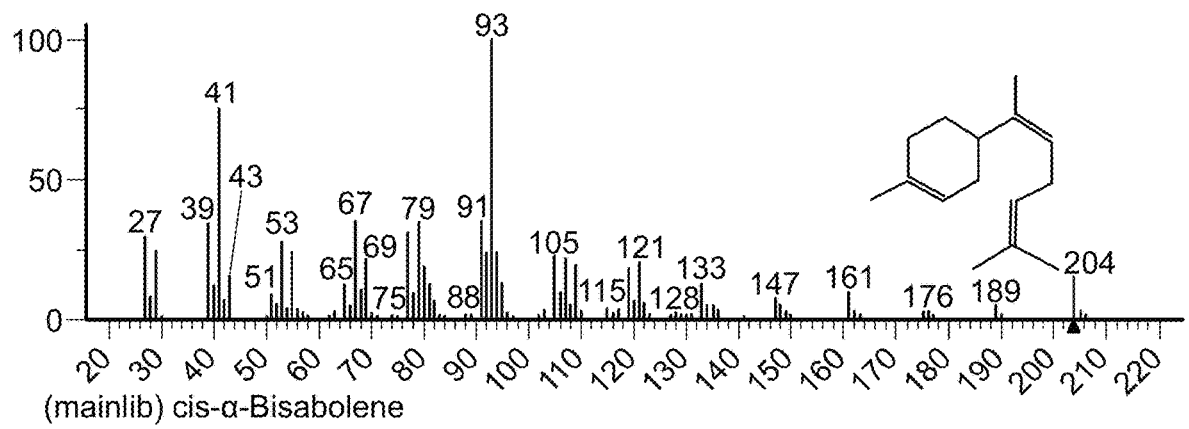
FIG. 1K. MS electron ionization fragmentation pattern for bisabolene, present in cultures of *Fusarium oxysporum, Fusarium proliferatum, Scedosporium apiospermum*.
Figure 1L:
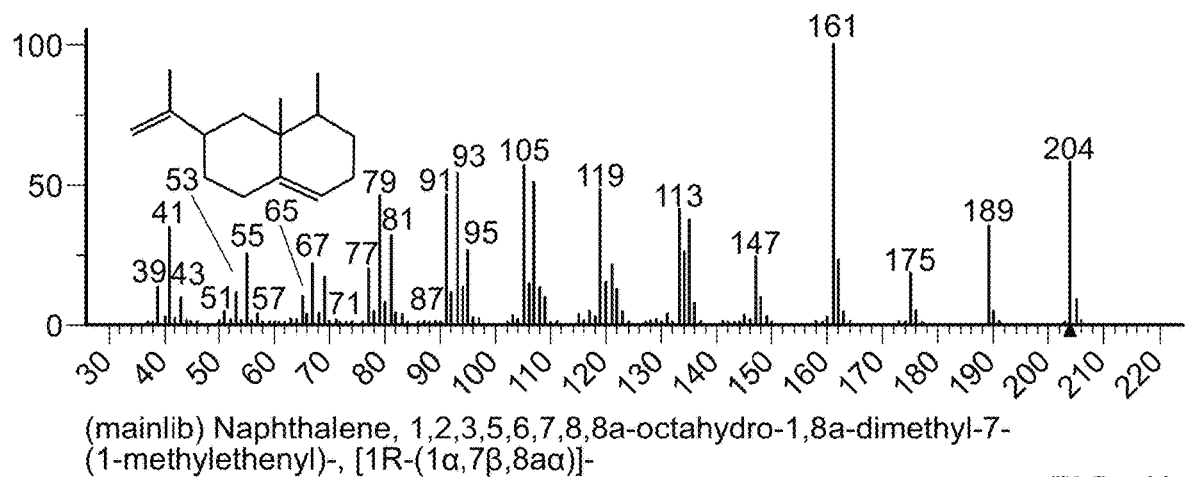
FIG. 1L. MS electron ionization fragmentation pattern for valencene, present in cultures of *Fusarium oxysporum, Fusarium proliferatum, Fusarium verticillioides*.
Figure 1M:
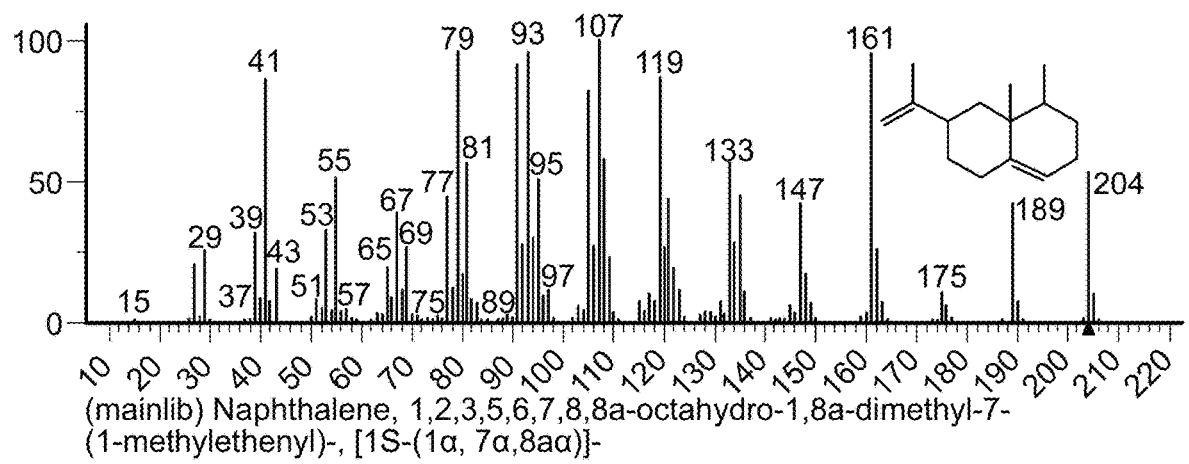
FIG. 1M. MS electron ionization fragmentation pattern for eremophilene, present in cultures of *Fusarium oxysporum, Fusarium proliferatum*.
Figure 1N:
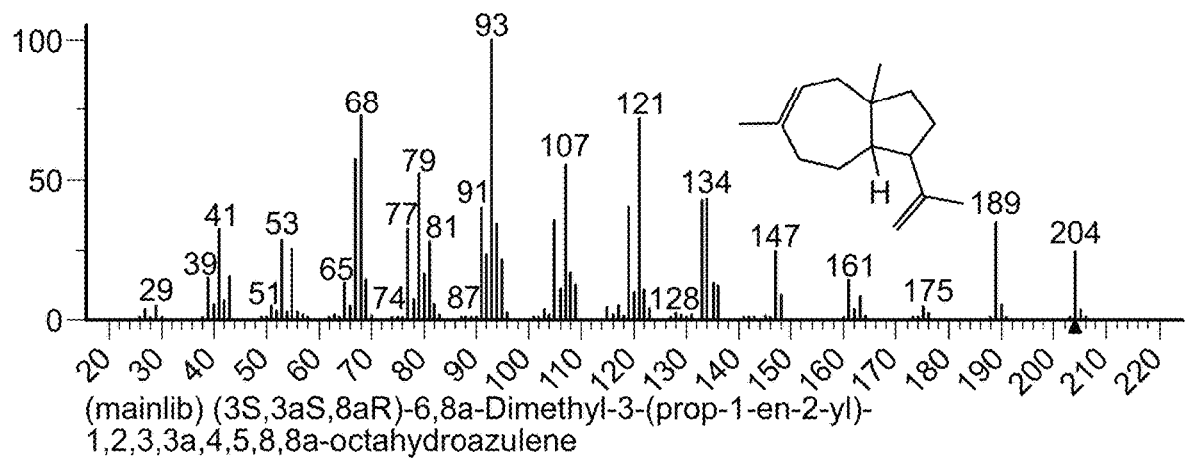
FIG. 1N. MS electron ionization fragmentation pattern for isodaucene, present in cultures of *Fusarium oxysporum, Fusarium proliferatum*.
Figure 1O:
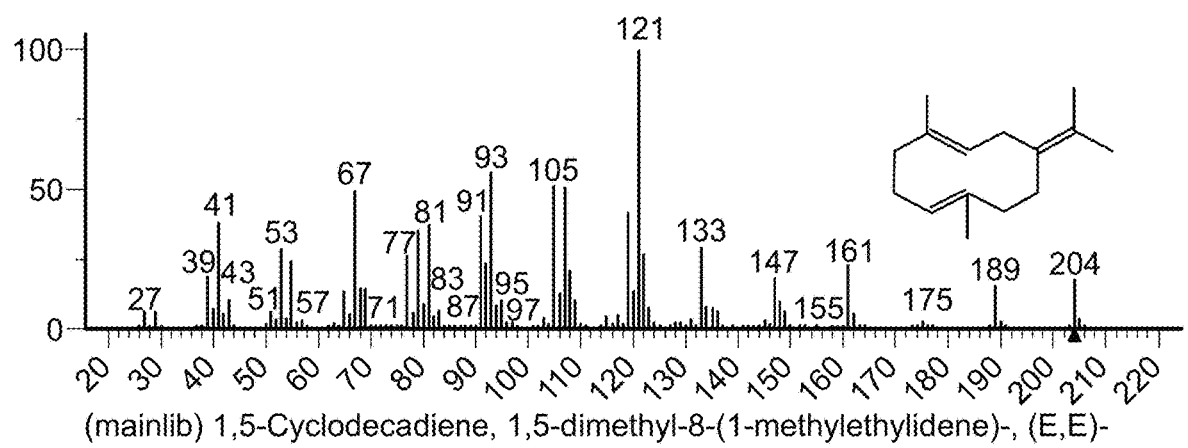
FIG. 1O. MS electron ionization fragmentation pattern for germacrene B, present in cultures of *Fusarium oxysporum, Fusarium proliferatum, Fusarium verticillioides*.
Figure 1P:
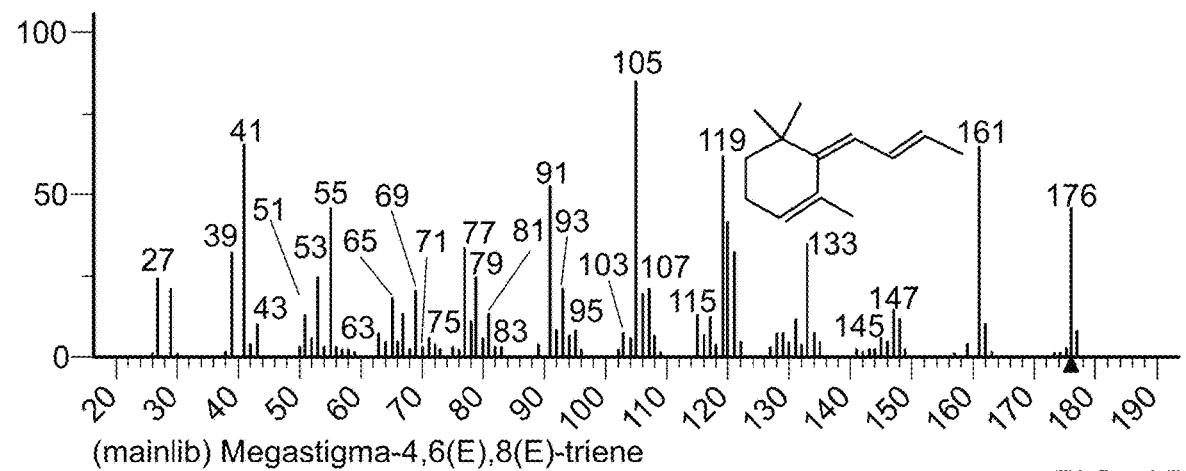
FIG. 1P. MS electron ionization fragmentation pattern for megastigma-4,6(Z),8(E)-triene, present in cultures of *Fusarium proliferatum*.
Figure 1Q:
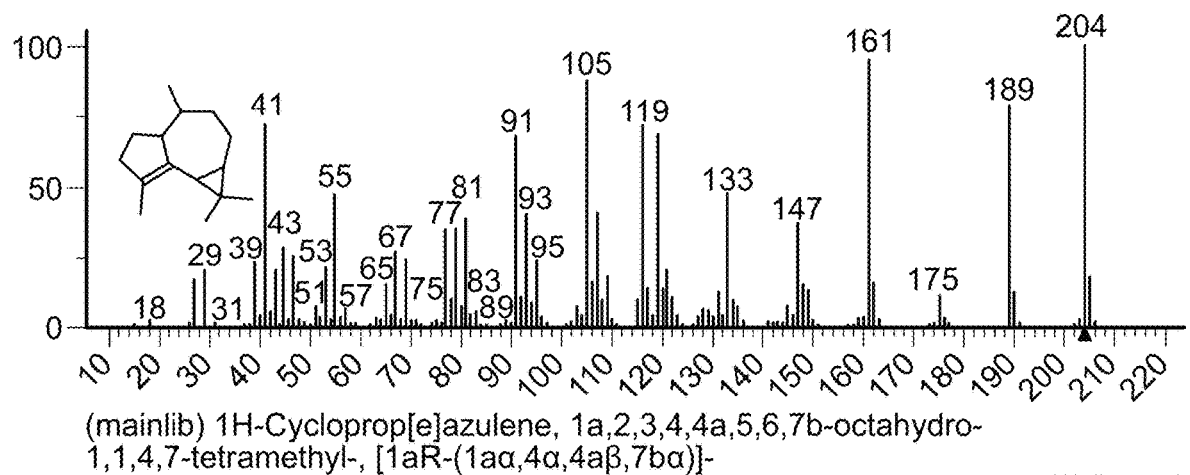
FIG. 1Q. MS electron ionization fragmentation pattern for α-gurjunene, present in cultures of *Fusarium proliferatum, Fusarium verticillioides, Scedosporium apiospermum*.
Figure 1R:
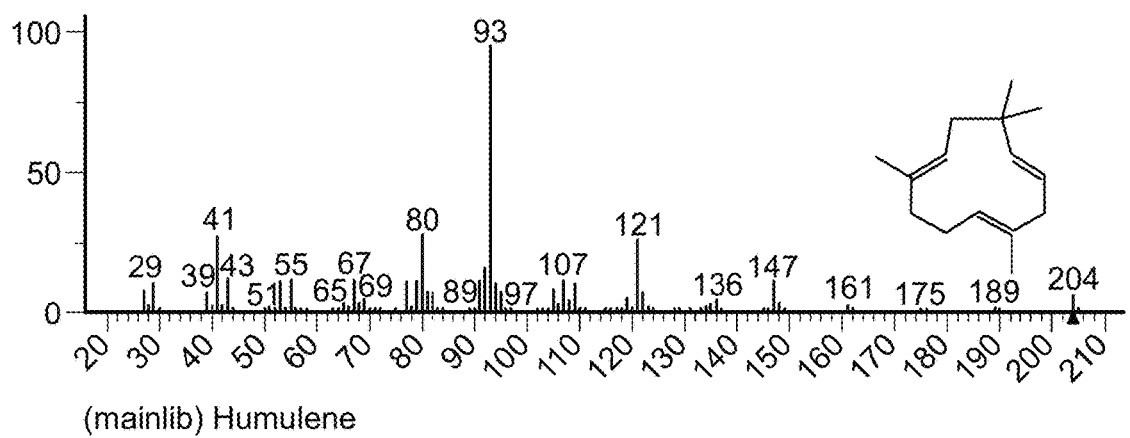
FIG. 1R. MS electron ionization fragmentation pattern for humulene, present in cultures of *Fusarium proliferatum, Fusarium solani, Fusarium verticillioides*.
Figure 1S:
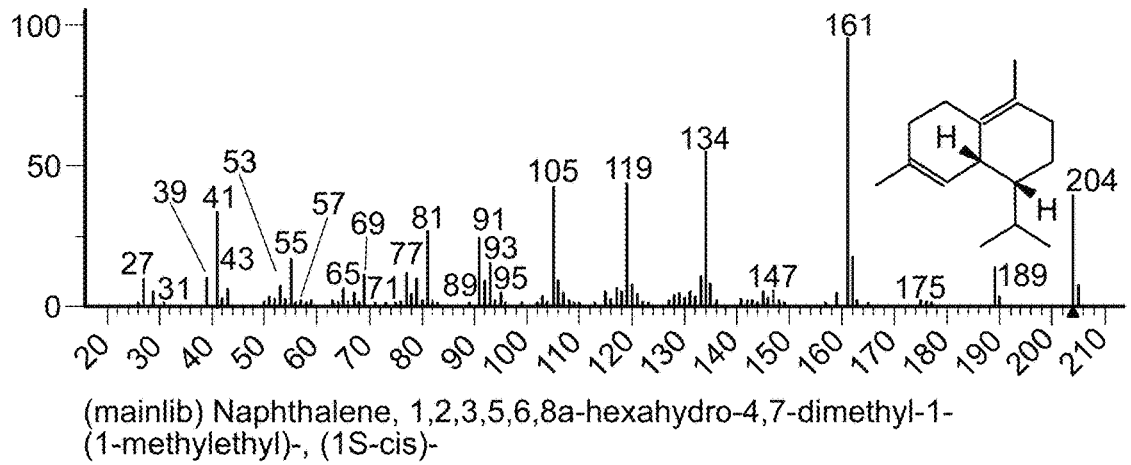
FIG. 1S. MS electron ionization fragmentation pattern for cadinene, present in cultures of *Fusarium proliferatum, Scedosporium apiospermum*.
Figure 1T:
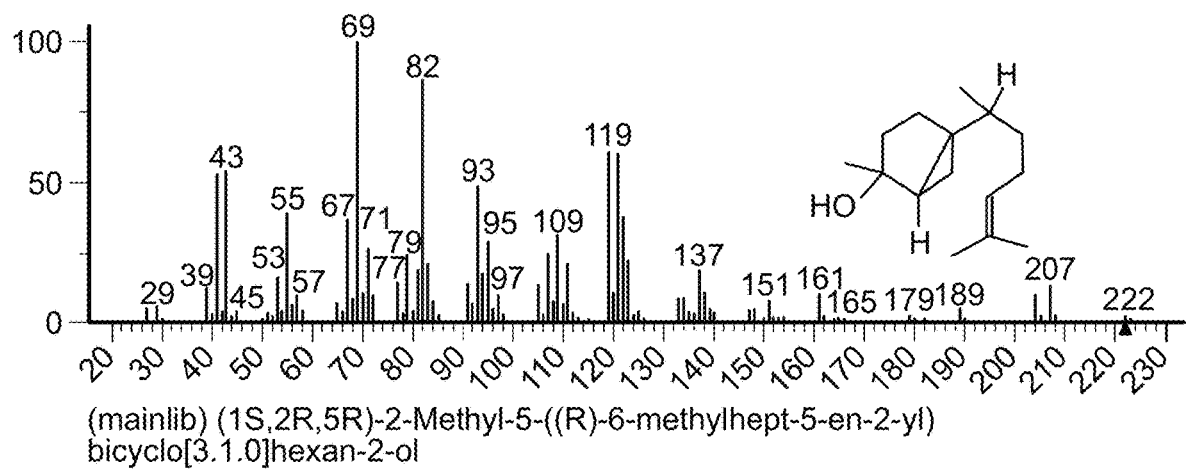
FIG. 1T. MS electron ionization fragmentation pattern for cis-sesquisabinene hydrate, present in cultures of *Fusarium proliferatum*.
Figure 1U:
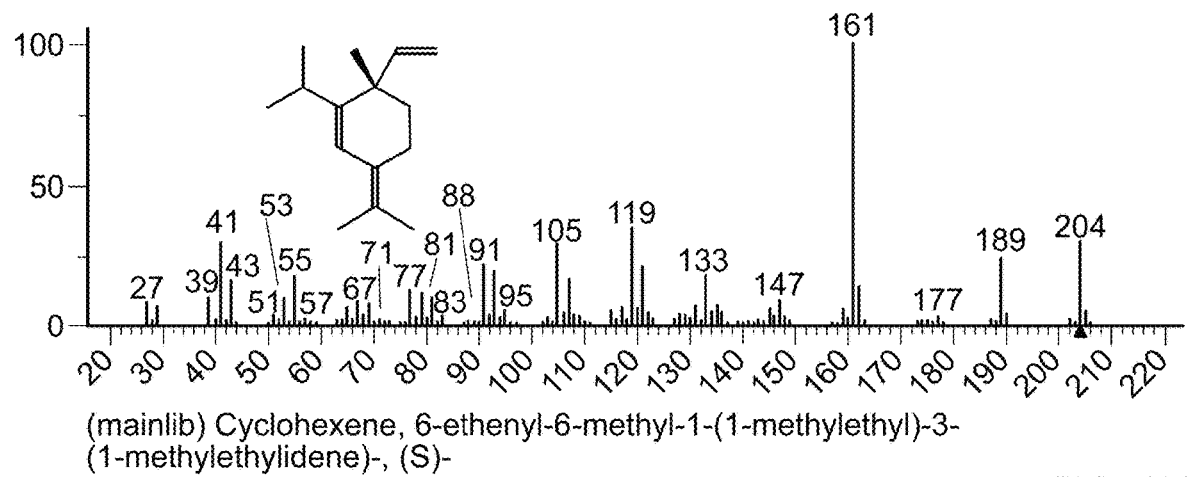
FIG. 1U. MS electron ionization fragmentation pattern for α-elemene, present in cultures of *Fusarium verticillioides*.
Figure 1V:
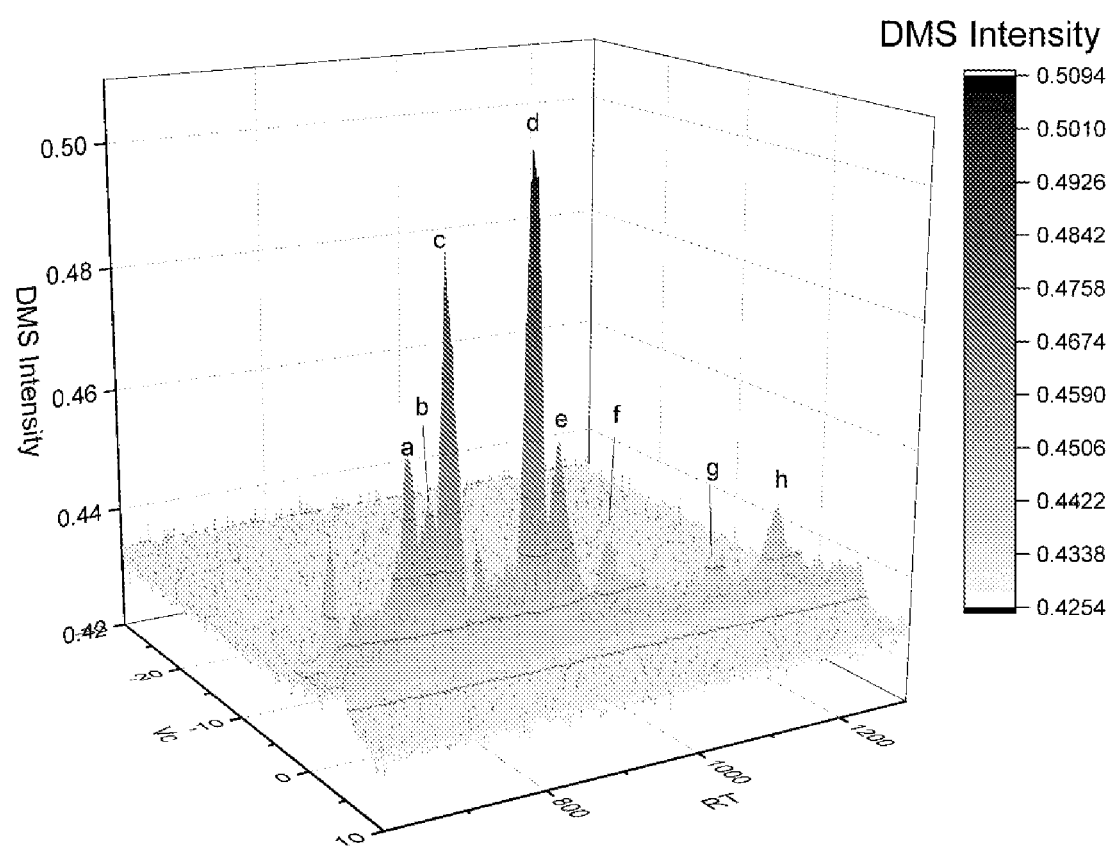
FIG. 1V. GC-differential mobility spectra of *F. oxysporum:* (a) cyclosativene (Vc=4V, RT=684.3 s), (b) 1H-indene, 2,3,3a,4-tetrahydro-3,3a,6-trimethyl-1-(1-methylethyl)- (Vc=4V, RT=709.99 s), (c) β-longipinene (Vc=4V, RT=733.43 s), (d) 3-Isopropyl-6,8a-dimethyl-1,2,4,5,8,8a-hexahydroazulene (Vc=4.4V, RT=844.90 s), (e) isocomene (Vc=4.4V, RT=873.5 s), (f) caryophyllene (Vc=4.4V, RT=939.0), (g) isodaucene (Vc=4.4V, RT=941.0), (h) germacrene B (Vc=4.4V, RT=1176.28).
Figure 1W:
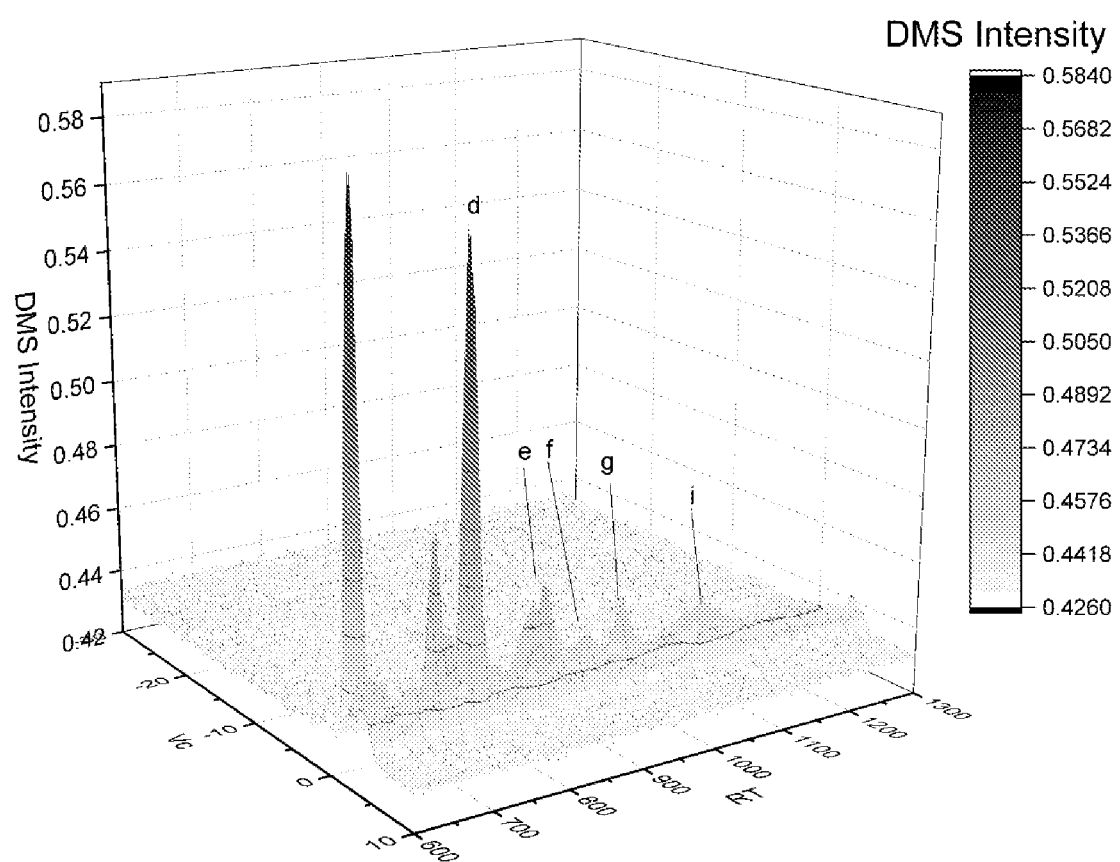
FIG. 1W. GC-differential mobility spectra of F proliferatum: (d) 3-Isopropyl-6,8a-dimethyl-1,2,4,5,8,8a-hexahydroazulene (Vc=4.4V, RT=844.90 s), (e) isocomene (Vc=4.4V, RT=873.5 s), (f) caryophyllene (Vc=4.4V, RT=944.1), (g) isodaucene (Vc=4.4V, RT=941.0), (i) cis-sesquisabinene hydrate B (Vc=4.4V, RT=1054.6).
Figure 1X:
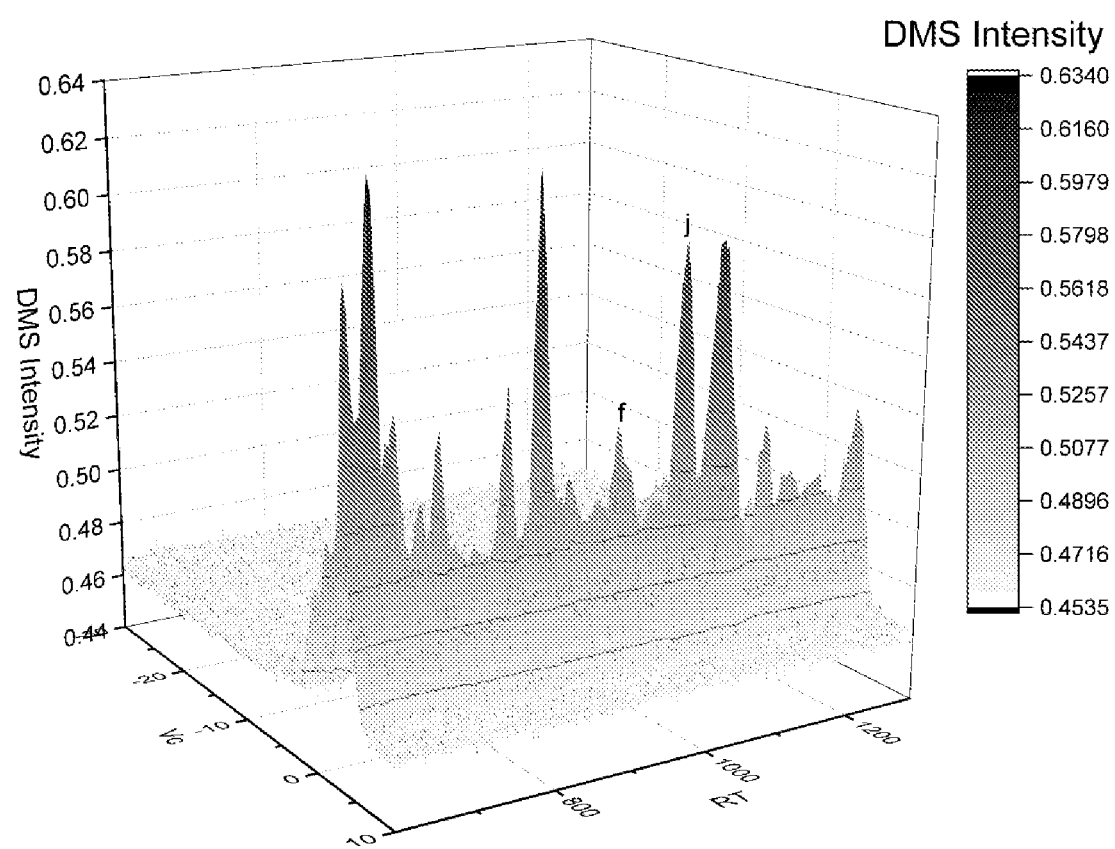
FIG. 1X. GC-differential mobility spectra of E solani: (f) caryophyllene (Vc=3.2V, RT=959.4), (j) humulene (Vc=3.6V, RT=1038.2).
Figure 1Y:
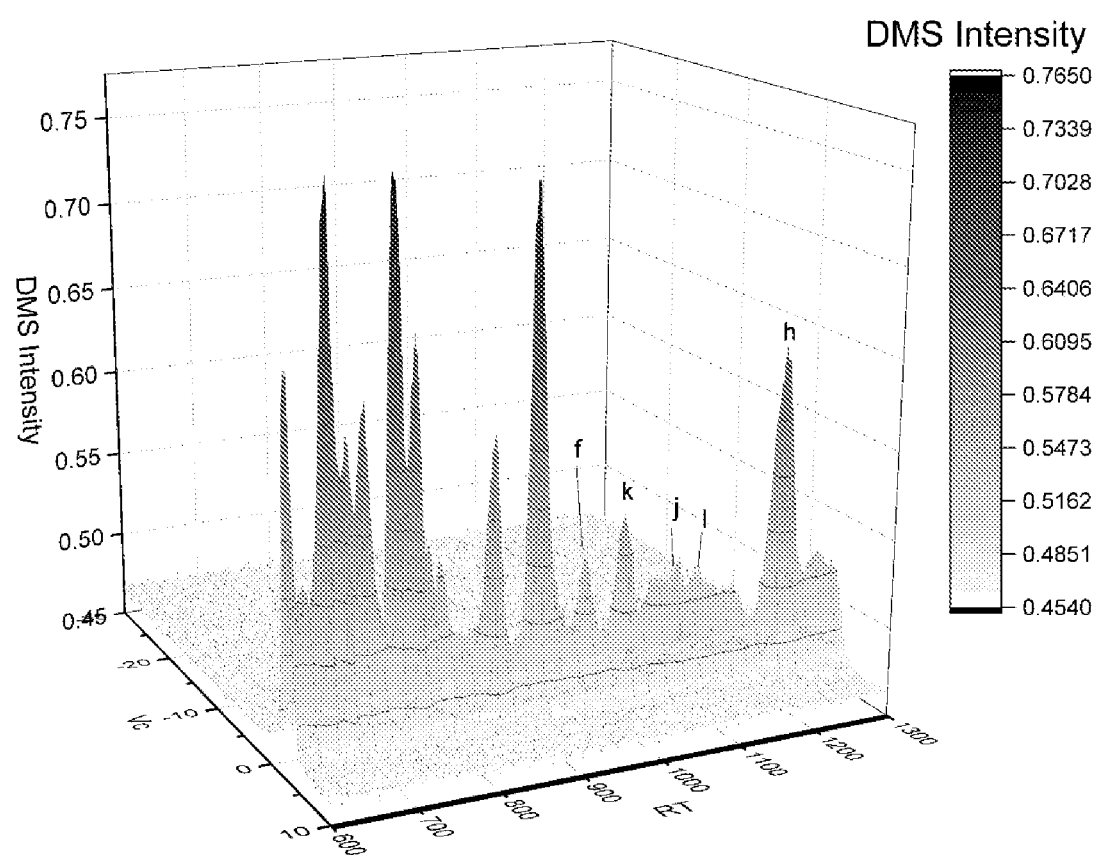
FIG. 1Y. GC-differential mobility spectra of E verticillioides: (f) caryophyllene (Vc=4.4V, RT=944.1), (g) isodaucene (Vc=4.4V, RT=941.0), (i) cis-sesquisabinene hydrate B (Vc=4.4V, RT=1054.6), (k) α-elemene (Vc=4.2V, RT=1006.2), (j) humulene (Vc=4V, RT=1048.4), (l) valencene (Vc=4, RT=1104.67), (h) germacrene B (Vc=4V, RT=1213.1).

Pathogenic molds produce VOCs as part of their normal metabolism. As described herein, the present inventors have identified unique, species-specific VOC profiles of *Fusarium, Scedosporium,* and *Lomentospora* species in vitro that can be used to discriminate these species from each other and from other molds. Some compounds identified in in vitro cultures were also present in the breath of patients, in addition to novel VOCs induced in vivo.

Detection of these unique VOC profiles can be harnessed for species-level identification of these and other mold species in the laboratory, and direct detection of these fungal volatile profiles in the breath of patients with suspected infections can be used for the rapid, noninvasive, highly accurate, and species-specific diagnosis. The methods and devices described herein, e.g., the GC-MS and DMS-based detection methods, can be adapted to a small, portable bedside breath gas detection system for real-time patient breath surveillance for this pattern of fungal metabolites, to allow for earlier diagnosis than currently possible, more rational test-based prescribing of antifungal medications, monitoring of clinical response to antifungal therapy, and ultimately, better patient outcomes.

As described herein, among other uses, these VOC profiles can be used for:
a. rapid, noninvasive, sensitive, and species-specific breath tests for the diagnosis of specific fungal infections and the discrimination of causes of infection in the growing population of immunocompromised patients at risk for invasive fungal infections;
b. surrogate marker demonstrating successful antifungal treatment of infection, and
c. rapid identification and antifungal susceptibility testing of these fungal species, e.g., in the microbiology laboratory, based on their VOC profile (i.e., the VOCs present in the sample).

*Fusariosis* and *Scedosporiosis*

The methods described herein can be used to detect or diagnose fusariosis and scedosporiosis (encompassing infections caused by *Scedosporium* spp. and *Lomentospora* spp.) in a subject, to select treatment and to treat fusariosis and scedosporiosis, and to monitor treatment of fusariosis and scedosporiosis.

*Scedosporium* and *Fusarium* spp. are environmental organisms. *Scedosporium* spp. are commonly found in soil and contaminated water. *S. apiospermum* and *S. prolificans* (a term encompassing *Lomentospora prolificans* and *S. inflatum*) are the two major species, and *Pseudallescheria boydii* is the teleomorph (sexual state) of the anamorph (asexual state) *S. apiospermum*. These pathogens can cause mycetoma, colonization of the airways, sinopulmonary infections, extrapulmonary localized infections, and disseminated infections. See, e.g., Cortez et al., Clin Microbiol Rev. 2008 January; 21(1): 157-197.

*Fusarium* spp. are found in contaminated water, soil and plants. The most commonly pathogenic species are *F. solani, F. oxysporum,* and *F. moniliforme*. The present methods can be used in the different forms of fusariosis and scedosporiosis, including localized (e.g., keratitis, onychomycosis, or mycetoma) as well as invasive, disseminated, pulmonary, meningeal and brain disseminated fusariosis (see, e.g., Araujo et al., "Mould Infections: A Global Threat to Immunocompromised Patients," In Ahmad et al., Eds., *Combating Fungal Infections: Problems and Remedy,* Springer Sci. Bus Media 2010; Walsh et al., Clinical Infectious Diseases 2008; 46:327-60; Milroy et al., J Clin Pathol. 1989 February; 42(2): 123-127). In some embodiments, the methods described herein can be used for subjects with invasive or pulmonary fusariosis or scedosporiosis.

Samples

The methods described herein can be performed on a gas or liquid sample. In some embodiments, the sample is exhaled breath directly from an individual or from a breathing machine such as a ventilator. Alternatively, the methods can be performed using headspace from a culture known or suspected to include *Scedosporium* or *Fusarium* species, e.g., commercially-available or lab-cultured species or species obtained from a primary sample from a subject, e.g., a clinical sample obtained by biopsy of the affected area (e.g., nasal biopsy, transthoracic percutaneous needle aspiration, or video assisted thoracoscopic biopsy) or bronchoalveolar lavage. The sample is maintained in a suitable growth medium to allow growth and metabolism of any *Scedosporium* or *Fusarium* species in the sample. In certain embodiments, the invention involves taking a clinical sample from a subject and placing it in media, for example, with microfluidics, or in culture, for example, with conventional culturing methods. The *Scedosporium* or *Fusarium* species, if present, are stimulated to metabolize. The headspace (gaseous phase) generated as a result of this metabolism can be collected and analyzed using a method described herein or known in the art, see, e.g., US20100291617. In some embodiments, the methods are performed directly on bronchoalveolar washings, obtained by bronchoscopy/bronchoalveolar lavage. In some embodiments, the sample is a gas, e.g., patient breath or gas from the headspace of an in vitro culture sample. Where headspace gas is used, the gas should be collected after the headspace has been in contact with the culture for a sufficient amount of time for the compounds to be present, preferably in an air-tight, sealed environment.

The VOCs can also be detected in a liquid sample, since they are expected to be there in equilibrium with the gaseous phase. Thus, in addition to or as an alternative, the samples assayed using the methods described herein can include a liquid, e.g., blood (e.g., plasma or serum), lymph, urine, tears, saliva, sputum, nasal mucus, phlegm (e.g., expectorate), or CSF from a subject (e.g., from a biological fluid that comes near or preferably into contact with the tissue or organ that is known or suspected to be infected with a *Scedosporium* or *Fusarium* species), or the liquid phase (e.g., supernatant) of an in vitro culture. In some embodiments, the sample comprises saliva from the subject.

Detection Methods

A number of methods known in the art can be used to detect the presence of the VOCs described herein in a sample. Exemplary methods (particularly for use with a gas sample) include gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; electrochemical sensors; photoacoustic equipment; laser-based equipment; electronic noses (bio-derived, surface coated); and various ionization techniques. See, e.g., US20100291617 and US20070003996. Preferred methods include ion mobility spectrometry (IMS) or differential mobility spectrometry (DMS).

In some embodiments, the methods described herein include the use of differential mobility spectrometry to detect VOCs in a sample. An exemplary micro-machined differential mobility spectrometer (DMS), developed for chemical and biological sensing applications, is currently available from Sionex Corporation. DMS has several features that make it an excellent platform for VOC analysis: it is quantitative, selective, and exquisitely sensitive, with a volatile detection limit in the parts-per-trillion range (Davis et al., In: 12th International Conference on Transducers, Solid-State Sensors, Actuators and Microsystems; 2003; p. 1233-8 vol.2; Miller et al., In: Solid-State Sensors and Actuators Workshop; 2000; Hilton Head, S.C.; 2000; Krebs et al., Sensors Journal, IEEE 2005; 5(4):696-703). Unlike mass spectrometry, which separates particles based on mass/charge ratios, DMS harnesses differences in ion mobility in low and high electric fields to achieve a gas-phase separation of ions at atmospheric pressure. DMS rapidly detects compounds that are difficult to resolve by other analytical techniques such as mass spectrometry in challenging matrices such as human breath (Kanu et al., J Mass Spectrom 2008; 43:1-22; Kanu et al., J Chromatogr A 2008; 1177:12-27; Luong J et al., J Chromatogr Sci 2006; 44:276-286; Nazarov et al., Anal Chem 2006; 7697-706; Kolakowski et al., Analyst 2007; 132:842-64).

DMS can be tuned to monitor specific ion masses, thus tailoring response characteristics to focus on various compounds of interest. It requires no reagents, generates the high fields required by the sensor using a small power supply, and has already been microfabricated, resulting in a small, portable machine that can be used at the bedside, with a turnaround time of several minutes. DMS has been used successfully in several commercial settings, including a hand-held, portable detector of trace levels of chemical warfare agents from General Dynamics (JUNO™) and airport explosives detectors from Thermo (see, e.g., U.S. Pat. No. 7,605,367). DMS technology has also been successfully applied to the characterization of unique VOCs produced by *Mycobacterium tuberculosis*, *Aspergillus* sp., and other bacteria (see, e.g., Fong et al., Anal Chem 2011; 83:1537-46; Shnayderman et al., Anal Chem 2005; 77:5930-7; WO 2014/039856; WO 2015/187938).

To perform a measurement using a DMS, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities. For other devices, measurements are performed using methods known in the art.

Additional non-limiting examples of systems that can be used in the present methods include those described in US20090078865; US20130168548; US20100291617 and US20070003996.

In some embodiments, the methods include obtaining a sample of ambient air and detecting the presence and/or levels of VOCs in the air, to provide a reference for subtraction of ambient VOCs.

A number of methods are known in the art for detecting the presence and/or levels of the VOCs in a liquid sample, including but not limited to chromatography (e.g., HPLC) and spectrophotometry (e.g., MS, LC-MS, MALDI-TOF, and other of the methods described above for gas-phase samples).

Combination Diagnostics

In some embodiments, the methods include performing an additional diagnostic test for fusariosis or scedosporiosis. A number of such tests are known in the art and include microbiology (direct staining and culture), histopathology, radiology/imaging, and serological and molecular biology. A positive result on one of these tests can provide further evidence supporting a diagnosis of fusariosis or scedosporiosis; see, e.g., Walsh et al., Clinical Infectious Diseases 2008; 46:327-60; Cortez et al., Clin Microbiol Rev. 2008 January; 21(1): 157-197.

Species Identification and Diagnosis

As described herein, the tested species each produce VOCs that can be used to identify them in a sample, e.g., in a sample comprising breath of a subject, or headspace from a culture suspected of comprising *Scedosporium* or *Fusarium* spp.; the culture can be, e.g., a culture of a biopsy from a subject, or a culture in a microbiology laboratory, e.g., a culture known or suspected of containing or being contaminated with a *Scedosporium* or *Fusarium* species. This identification can be used to diagnose a subject with the specific species of *Scedosporium* or *Fusarium*, allowing for the administration of species-specific treatments, e.g., as described below.

Thus, the methods described herein can include obtaining a sample comprising breath of a subject, or headspace from a culture suspected of comprising *Scedosporium* or *Fusarium*, and detecting and identifying the VOCs in the sample. For example, the methods can include detecting the presence of one, two, three, or more VOCs as shown in Tables 1 and 2 in the sample. The presence of one, two, three, or more of the VOCs indicates the presence of the corresponding fungus in the sample (and thus a fungal infection in cases where the sample is from a subject). In some embodiments, e.g., where a VOC associated with more than one species is present, at least one or two other VOCs must also be present for a positive species identification, and a species-specific diagnosis, to be made.

TABLE 1

| *Scedosporium* | |
| --- | --- |
| *Scedosporium* Species | VOC |
| *S. apiospermum* (in vitro) | α-longipinene, β-longipinene, α-gurjunene, β-gurjunene, γ-gurjunene, isocomene, trans-α-bergamotene, himachalene, bisabolene, cadinene,selina-5,11-diene, aromandendrene, alloaromadendrene, naphthalene, 1,2,4a,5,6,8a-hexahydro-4,7-dimethyl-1-(1-methylethyl)-, selinene, epizonarene |
| *S. apiospermum* (in patient breath) | 1H-Indene, 2,3,3a,4-tetrahydro-3,3a,6-trimethyl-1-(1-methylethyl)-, β-gurjunene, β-longipinene, isocomene, β-guaiene |
| *Lomentospora prolificans* | Himachalene, γ-gurjunene |
| *Scedosporium boydii* | γ-gurjunene |

TABLE 2

| Fusarium Species | VOC |
| --- | --- |
| F. oxysporum | cyclosativene,<br>β-longipinene,<br>3-isopropyl-6,8a-dimethyl-1,2,4,5,8,8a-hexahydroazulene,<br>isocomene,<br>γ-elemene,<br>trans-α-bergamotene,<br>himachalene,<br>caryophyllene,<br>santalene,<br>bisabolene,<br>valencene,<br>eremophilene,<br>isodaucene, and<br>germacrene B |
| F. proliferatum | megastigma-4,6(Z),8(E)-triene,<br>β-longipinene,<br>3-isopropyl-6,8a-dimethyl-1,2,4,5,8,8a-hexahydroazulene,<br>isocomene,<br>γ-elemene,<br>α-gurjunene,<br>trans-α-bergamotene,<br>caryophyllene,<br>santalene,<br>bisabolene,<br>humulene,<br>cadinene,<br>valencene,<br>eremophilene,<br>isodaucene,<br>sesquisabinene hydrate, and<br>germacrene B |
| Fusarium solani | caryophyllene<br>humulene |
| Fusarium verticillioides | α-gurjunene,<br>γ-elemene,<br>trans-α-bergamotene,<br>himachalene,<br>caryophyllene,<br>α-elemene,<br>santalene,<br>humulene,<br>valencene, and<br>germacrene B |

Methods of Treatment

The methods described herein can be used to select a treatment for a subject, and can optionally include administering the treatment to a subject. When a subject has been diagnosed by a method described herein as having fusariosis or scedosporiosis, then a treatment comprising administration of a therapeutically effective amount of an antifungal compound, or a combination thereof, can be administered.

A number of antifungal compounds are known in the art and under development. At present, deoxycholate amphotericin B (D-AMB) and its lipid formulations (AMB lipid complex (ABLC), liposomal amphotericin B (LAMB), and Amphotericin B cholesteryl sulfate complex (AMB colloidal dispersion, ABCD)); azole compounds (itraconazole, voriconazole, posaconazole); and echinocandins (caspofungin, micafungin, anidulafungin) are in clinical use. For detailed information on treatment of fungal diseases, see, e.g., Walsh et al., Clinical Infectious Diseases 2008; 46:327-60; Cortez et al., Clin Microbiol Rev. 2008 Jan; 21(1):157-197; and Araujo et al., "Mould Infections: A Global Threat to Immunocompromised Patients," In Ahmad et al., Eds., Combating Fungal Infections: Problems and Remedy, Springer Sci. Bus Media 2010.

In some embodiments, the methods include selecting and optionally administering an azole antifungal, e.g., itraconazole (ITR), voriconazole (VOR), posaconazole (POS), ravuconazole (RAV), or isavuconazole (ISA), or an amphotericin B (AMB) formulation as described above, to a subject identified by a method described herein as having an infection with Scedosporium or Fusarium. In some embodiments, the methods include administering an echinocandin, e.g., caspofungin, micafungin or anidulafungin, e.g., alone or in combination with an azole (e.g., voriconazole) or AMB. In some embodiments, the methods include administration of an azole (e.g., voriconazole) or AMB with an immunotherapy, e.g., neutrophils (polymorphonuclear leukocytes; see, e.g., Gil-Lamaignere et al., J. Antimicrob. Chemother. 50(6), 1027-1030 (2002) and Gil-Lamaignere et al., Antimicrob. Agents Chemother. 46(7), 2234-2237 (2002)); Inteferon gamma and/or granulocyte-macrophage colony-stimulating factor (see Gil-Lamaignere et al., Med. Mycol. 43(3), 253-260 (2005); Ortoneda et al., J. Antimicrob. Chemother. 49(3), 525-529 (2002)). See, e.g., Antachopoulos et al., Immunotherapy. 2012; 4(1):107-120.

In some embodiments, where the species of Scedosporium or Fusarium is determined, the methods include selecting a treatment based on the species present. For example, for a subject who has S. prolificans, the methods can include administering an azole compound (e.g., ITR, VOR, POS, RAV, or ISA), e.g., VOR, in combination with hexadecylphospocholine (miltefosine) and terbinafine and voriconazole (Kesson et al., Infect. Dis. 48(9), 1257-1261 (2009)); or voriconazole and caspofungin, as well as locally applied polyhexamethylene biguanide (Steinbach et al., J. Clin. Microbiol. 41(8), 3981-3985 (2003)). In some embodiments, a subject diagnosed with an infection with F. solani or F. verticilloides is administered AMB but not voriconazole. In some embodiments, a subject diagnosed with fusariosis is administered terbinafine.

In some embodiments, the methods described herein can be used to determine susceptibility of a fungal species, e.g., to treatment with a known or suspected antifungal, e.g., in the microbiology laboratory. A sample suspected or known to include Scedosporium or Fusarium from a subject is obtained and cultured as described above, e.g., under conditions mimicking the in vivo environment, and then exposed to a potential treatment (e.g., a known or experimental treatment). After exposure to the treatment, the VOCs present in the headspace of the culture are sampled (e.g., the VOCs shown in Table 1 and 2). If the treatment decreases VOCs as compared to a reference level (e.g., a level of VOCs in the headspace before exposure to the treatment), then the Scedosporium or Fusarium in the sample is considered susceptible to the treatment. In this case, the treatment is likely to be effective in treating fusariosis or scedosporiosis in the subject; the treatment can be selected and optionally administered to subject.

Monitoring Treatment Efficacy

As described herein, successful treatment of a Scedosporium or Fusarium infection results in a decrease in fungal VOCs. Thus, the methods can include repeated assays of VOC levels in a subject, e.g., before, during, and after administration of a treatment for scedosporiosis or fusariosis. In some embodiments, levels of one, two, three, or more VOCs listed in Table 1 and/or Table 2 are determined. A decrease in VOC levels would indicate that the treatment has been successful. In some embodiments, the subject has invasive scedosporiosis and levels of one, two, or all three of β-gurjunene, β-longipinene, and isocomene are determined in a sample; in some embodiments, one, two, three, four, or more of 1H-Indene; 2,3,3a,4-tetrahydro-3,3a,6-trimethyl-1-(1-methylethyl)-; β-gurjunene, β-longipinene, isocomene, and β-guaiene are determined in a sample.

Methods of Identifying Novel Antifungal Agents

Included herein are methods for screening test compounds, e.g., polypeptides, polynucleotides, inorganic or organic large or small molecule test compounds, to identify agents useful in the treatment of *Scedosporium* or *Fusarium* infections.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising one or more *Scedosporium* or *Fusarium* species, and the ability of the test compound to decrease levels of a VOC as described herein in the headspace of the culture is determined.

In some embodiments, the test sample is, or is derived from (e.g., a sample taken from) an in vivo model of a disorder as described herein. For example, an animal model, e.g., a rodent (such as a rat or mouse) that has been infected with one or more *Scedosporium* or *Fusarium* species can be used.

A test compound that has been screened by a method described herein and determined to decrease VOCs, can be considered a candidate compound. A candidate compound that has been screened, e.g., in an in vivo model of a disorder, e.g., a rodent infected with one or more *Scedosporium* or *Fusarium* species, and determined to decrease VOCs in a sample comprising breath from the infected animal model or headspace from a culture of a sample from the infected animal model, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that decrease fungal VOCs in an animal model) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating fusariosis or scedosporiosis. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of fusariosis or scedosporiosis, as described herein. The animal can be monitored for a change in the disorder, e.g., for an improvement in a parameter of the disorder, e.g., a parameter related to clinical outcome. In some embodiments, the parameter is VOCs or survival, and an improvement would be a reduction in VOCs or an increase in survival. In some embodiments, the subject is a human, e.g., a human with fusariosis or scedosporiosis and the parameter is levels of fungal VOCs or survival.

EXAMPLES

The invention is further described in the following examples, which do not limit the scope of the invention described in the claims.

Example 1

Volatile Metabolite Signatures for the Diagnosis and Treatment of Common Pathogenic *Fusarium, Scedosporium* and *Lomentospora* Species In Vitro Testing of *Fusarium, Scedosporium,* and *Lomentospora* species: We characterized the in vitro volatile metabolite profiles of clinical isolates of each of these species, including *Fusarium solani* (N=3), *Fusarium proliferatum* (N=5), *Fusarium oxysporum* (N=7), *Fusarium verticillioides* (N=4), *Scedosporium apiospermum* (N=8), *Lomentospora prolificans* (N=6) and *Pseudallescheria boydii* (N=4). All isolates had molecular confirmation of their species identity by ITS and D1/D2 sequencing (Fungus Testing Laboratory, University of Texas Health Science Center San Antonio; San Antonio, Tex.).

Fungal Culture and Headspace Extraction Conditions: We inoculated $10^6$ conidia from each species into 5 mL of YPD broth (Teknova, Hollister, Calif.) in a 20-mL glass vial sealed with an airtight cap incorporating a silicone septum (Restek Corporation, Bellefonte, Pa.), with concurrent media controls, in sets of 4 technical replicates each for each fungal species. We incubated each vial at 37° C. for 72-96 hours in an orbital shaker at 250 rpm to promote hyphal growth and prevent conidiation. After heating each vial to 80° C. for 30 minutes to increase the concentration of sesquiterpene metabolites in the gas phase of the vial, we adsorbed headspace gas over 4 minutes per sample onto thermal desorption tubes containing tandem beds of Tenax TA (200 mg), Carbograph 1 TD (100 mg), and Carboxen 1003 (100 mg) (Markes International, Llantrisant, United Kingdom), to retain polar and nonpolar VOCs over a wide range of boiling points.

In Vivo Testing of Mucorales species: We collected breath samples from patients with suspected invasive fungal disease over 4 minutes per sample onto thermal desorption tubes containing tandem beds of Tenax TA (200 mg), Carbograph 1 TD (100 mg), and Carboxen 1003 (100 mg) (Markes International, Llantrisant, United Kingdom).

GC-MS/MS methods: We thermally desorbed volatile metabolites from fungal culture headspace and from breath onto an automated thermal desorption unit (TD-100, Markes International) at 290° C. for 5 minutes with helium carrier gas at a flow rate of 40 mL/min. Volatile analytes were concentrated onto a TD-100 air toxics cold trap (U-T15ATA-2S, Markes International), which was rapidly heated to 300° C. to deliver volatile metabolites, with a 10:1 split ratio, to a Vf-624 ms capillary column (30 m×0.25 mm, 6% cyanopropyl/phenyl, 94% polydimethylsiloxane, film thickness 1.4 µm, Agilent Technologies, Santa Clara, Calif.) with a gas chromatograph (GC) inlet temperature of 250° C. and a GC temperature program of 40° C. for 3 minutes raised to 70° C. at a rate of 5° C. per minute and held for 3 minutes, raised to 203° C. at 7° C. per minute and held for 4 minutes, then rapidly raised to 270° C. and held for 5 minutes. A triple quadrupole mass spectrometry (MS) detector (Agilent 7000A, Agilent Technologies, Santa Clara, Calif.) was used to analyze and identify VOCs, with a MS source temperature of 230° C., MS quad temperature of 150° C., and an electron ionization parameter of 1412 eV. A mass range m/z 40-550 was measured with a threshold of 150. We used identical conditions for our GC-MS/MS analysis after recollecting each sample onto the same sorbent tube, filtering for precursor ion 204>161, 133, 119, 107, and 93 with a voltage of 5 and 15 eV, 204>, with a voltage of 5 and 15 eV, 202>159 and 145 with a voltage of 5 and 15 eV, and 194>136 and 105 with a voltage of 5 and 15 eV.

Confirmation of metabolite identity: We used the National Institute of Standards and Technology (NIST) 14 Mass Spectral Library (Scientific Instrument Services, Ringoes, N.J.) for provisional identification of sesquiterpene/sesquiterpene derivative GC-MS peaks in the total ion chromatogram of each culture and media control, with comparison to Kovats retention indices.

GC-DMS methods: We extracted the headspace volatile organic compounds of heated cultures of these species over 180-240 seconds onto a GC-DMS Microanalyzer instrument equipped with a multibed sorbent tube and 30 meter, 0.25 mm internal diameter Vf624 GC column, at a pump rate of 100 mL/minute, repressurizing each headspace vial with an equal flow (100 mL/min) of high-purity nitrogen gas for the duration of each headspace extraction. Using a sorbent trap temperature program of 40° C. at baseline, ramping quickly from 0-5 seconds to 300° C. and staying at 300° C. for 60 seconds to allow release of volatile organic analytes retained on the sorbent tube onto the GC column, followed by a GC thermal program of 60° C. at baseline, ramping from 60° C. to 160° C. over 90 seconds, and remaining at 160° C. from 90-1300 seconds, with detection of analyte ions on the DMS detector. We used a scanning method with a starting compensation voltage of −30 and an ending compensation voltage of 10 with 101 steps of 0.4V each (each step duration was 10 milliseconds with a step settle time of 3 ms and each scan duration 1.01 seconds), a sensor temperature of 25° C., and a Rf voltage of 1200V, with recording of positive and negative DMS spectra by the detector. We also analyzed breath samples, collecting 240 seconds of regular tidal breathing directly onto this GC-DMS Microanalyzer instrument, using a GC thermal program of 60° C. at baseline, ramping from 60° C. to 150° C. over 90 seconds, and remaining at 150° C. from 90-1800 seconds.

Results:

In vitro cultures: In *Fusarium,* we identified some unique (species-specific) and many shared (among members of the genus) volatile secondary sesquiterpene metabolites by GC-MS, with corresponding identification of these species-specific metabolite signatures by GC-DMS. *F. oxysporum* produced a complex sesquiterpene profile of cyclosativene, β-longipinene, 3-isopropyl-6,8a-dimethyl-1,2,4,5,8,8a-hexahydroazulene, isocomene, γ-elemene, trans-α-bergamotene, himachalene, caryophyllene, santalene, bisabolene, valencene, eremophilene, isodaucene, and germacrene B (FIG. 1A-O). *F. proliferatum* produced a signature of megastigma-4,6(Z),8(E)-triene, β-longipinene, 3-isopropyl-6,8a-dimethyl-1,2,4,5,8,8a-hexahydroazulene, isocomene, γ-elemene, α-gurjunene, trans-α-bergamotene, caryophyllene, santalene, bisabolene, humulene, cadinene, valencene, eremophilene, isodaucene, sesquisabinene hydrate, and germacrene B (FIGS. 1A, 1C-1O; 1T), and *Fusarium solani* emitted caryophyllene and humulene (FIGS. 1A, 1I, 1R). *Fusarium verticillioides* emitted a profile of α-gurjunene, γ-elemene, trans-α-bergamotene, himachalene, caryophyllene, α-elemene, santalene, humulene, valencene, and germacrene B (FIGS. 1A, 1F-1J, 1L, 1O, 1Q-1R, 1U).

Figure 2A:
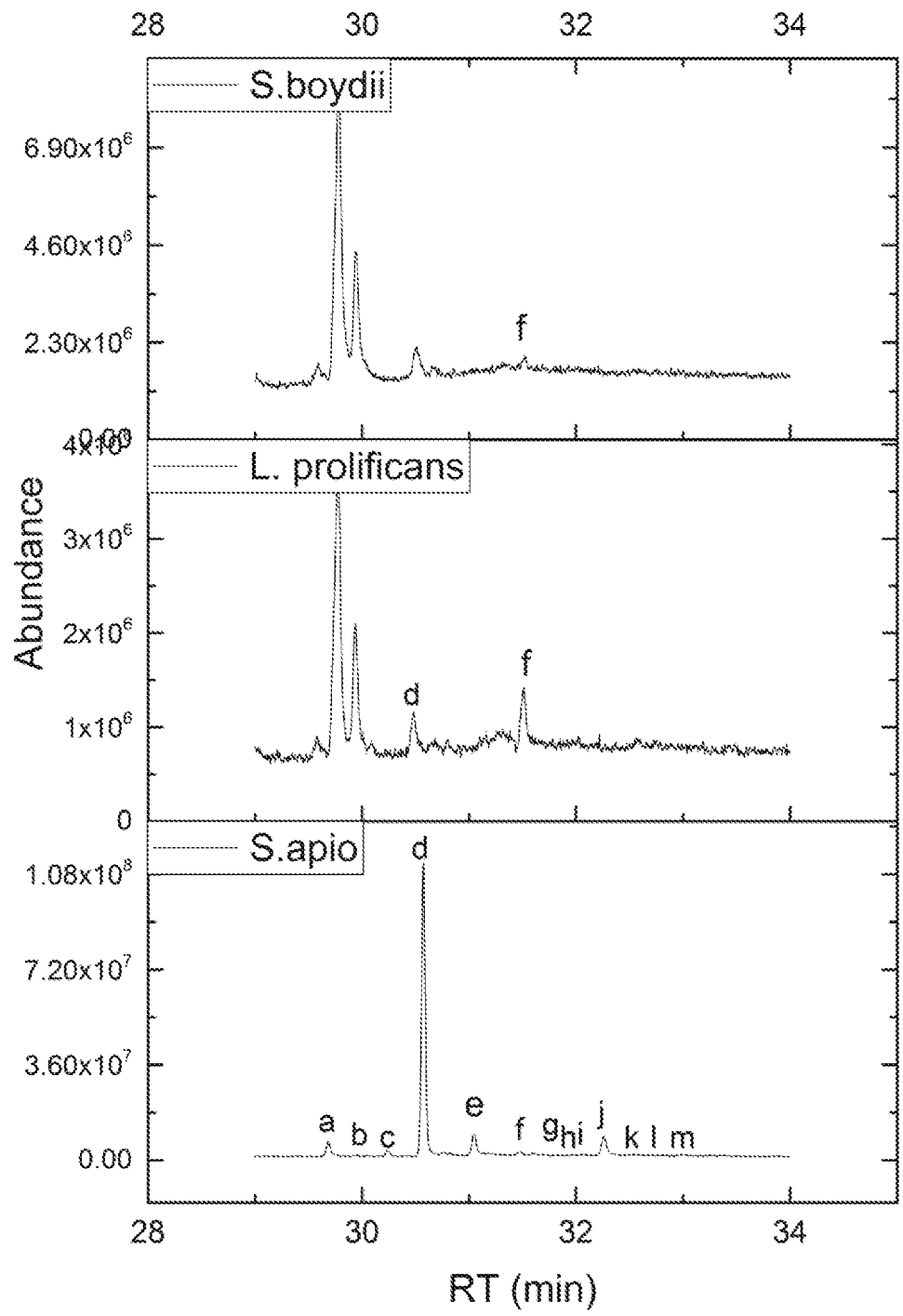
FIG. 2A. Sample GC-MS total ion chromatograms of headspace gas from cultures of *Scedosporium boydii, Lomentospora prolificans*, and *Scedosporium apiospermum;* (a) β-longipinene, (b) β-gurjunene, (c) β-longipinene, (d) aromandendrene, (e) himachalene, (f) selina-5,11-diene, (g) trans-α-bergamotene, (h) γ-gurjunene, (i) naphthalene, 1,2,4a,5,6,8a-hexahydro-4,7-dimethyl-1-(1-methylethyl)-, (j) selinene, (k) bisabolene, (l) cadinene, (m) epizonarene; full GC-MS fragmentation patterns as outlined below (and for some overlapping with *Fusarium* species, outlined above).
Figure 2B:
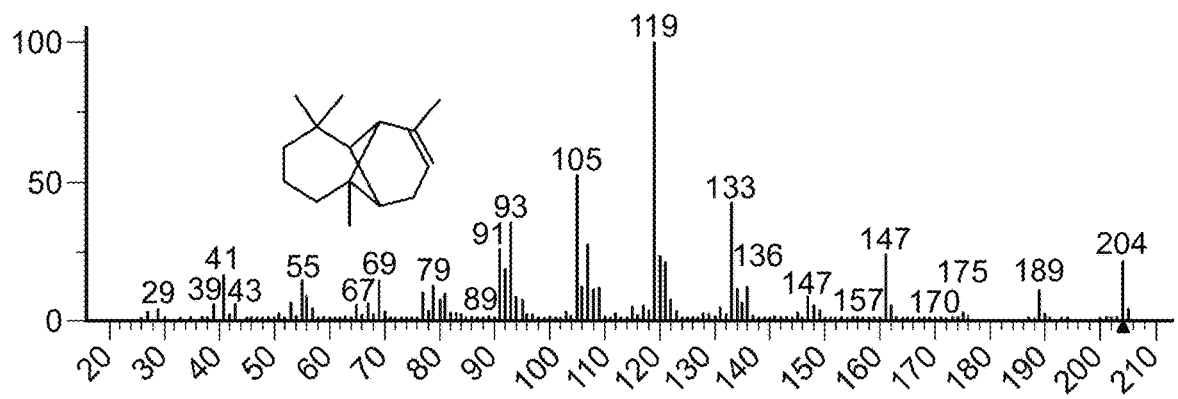
FIG. 2B. MS electron ionization fragmentation pattern for α-longipinene, present in cultures of *Scedosporium apiospermum*.
Figure 2C:
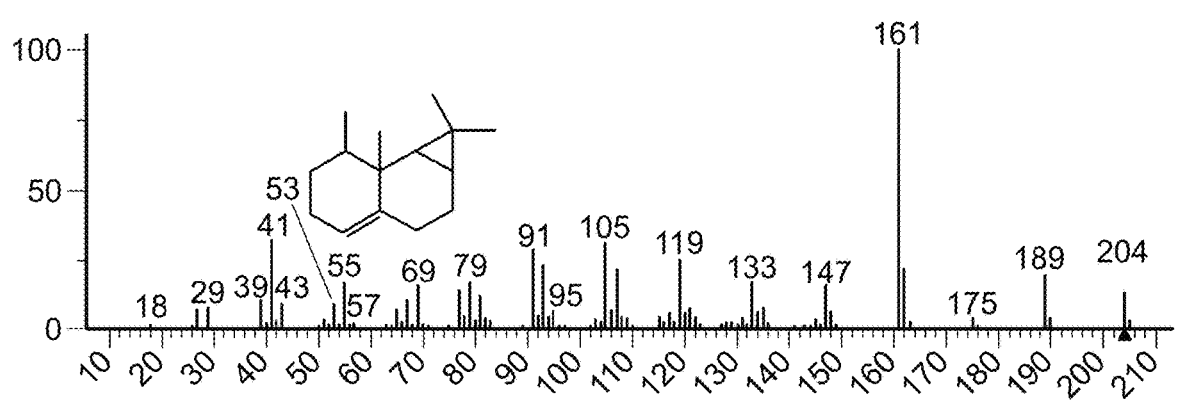
FIG. 2C. MS electron ionization fragmentation pattern for β-gurjunene, present in cultures of *Scedosporium apiospermum* and in the breath of 2 patients with disseminated *S. apiospermum* infection.
Figure 2D:
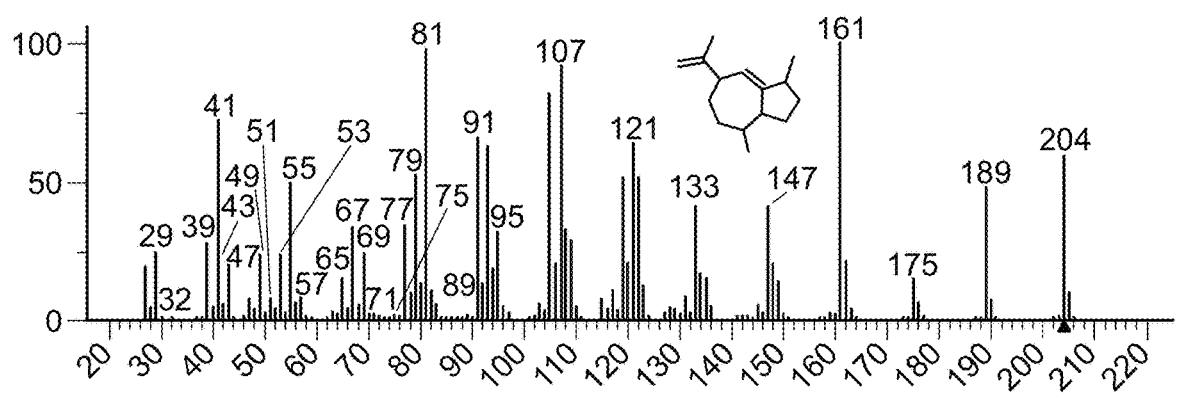
FIG. 2D. MS electron ionization fragmentation pattern for γ-gurjunene, present in cultures of *Scedosporium apiospermum, Lomentospora prolificans*.
Figure 2E:
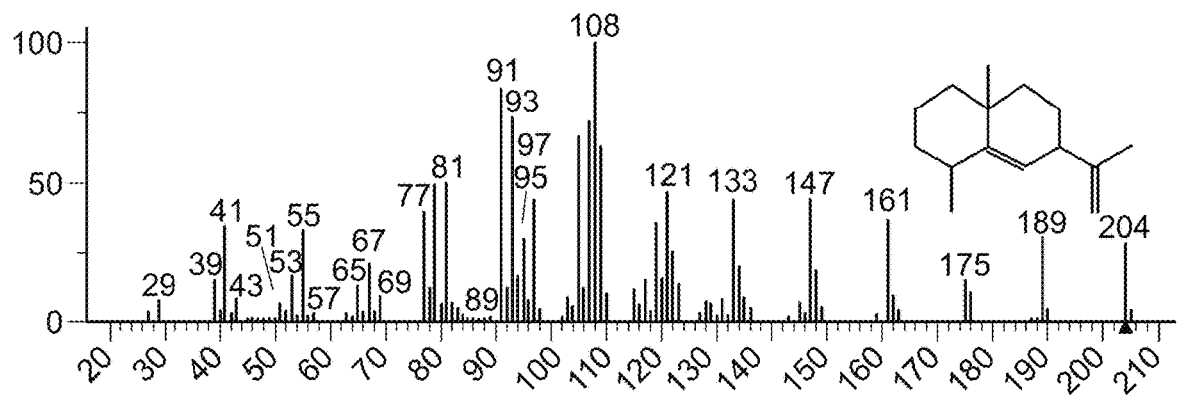
FIG. 2E. MS electron ionization fragmentation pattern for selina-5,11-diene, present in cultures of *Scedosporium apiospermum*.
Figure 2F:
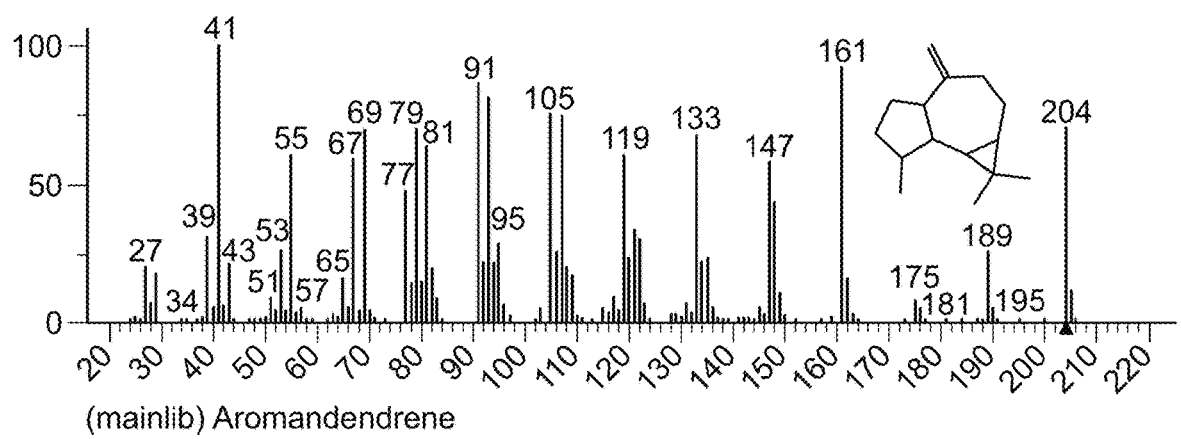
FIG. 2F. MS electron ionization fragmentation pattern for aromandendrene, present in cultures of *Scedosporium apiospermum*.
Figure 2G:
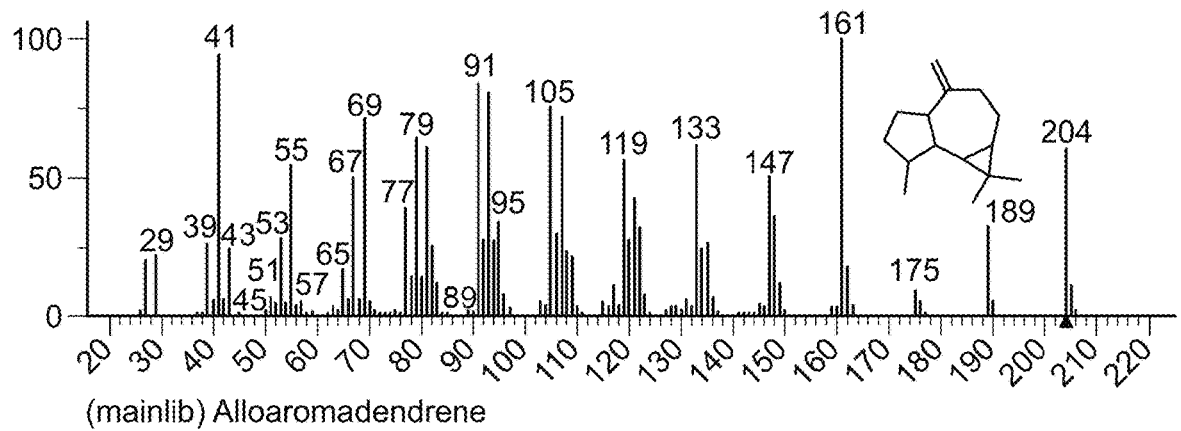
FIG. 2G. MS electron ionization fragmentation pattern for alloaromadendrene, present in cultures of *Scedosporium apiospermum*.
Figure 2H:
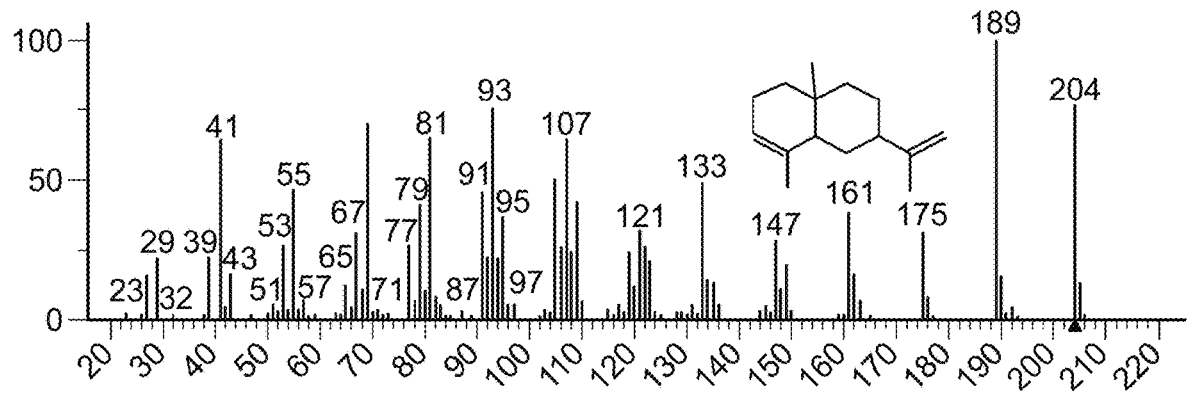
FIG. 2H. MS electron ionization fragmentation pattern for naphthalene, 1,2,4a,5,6,8a-hexahydro-4,7-dimethyl-1-(1-methylethyl)-, present in cultures of *Scedosporium apiospermum*.
Figure 2I:
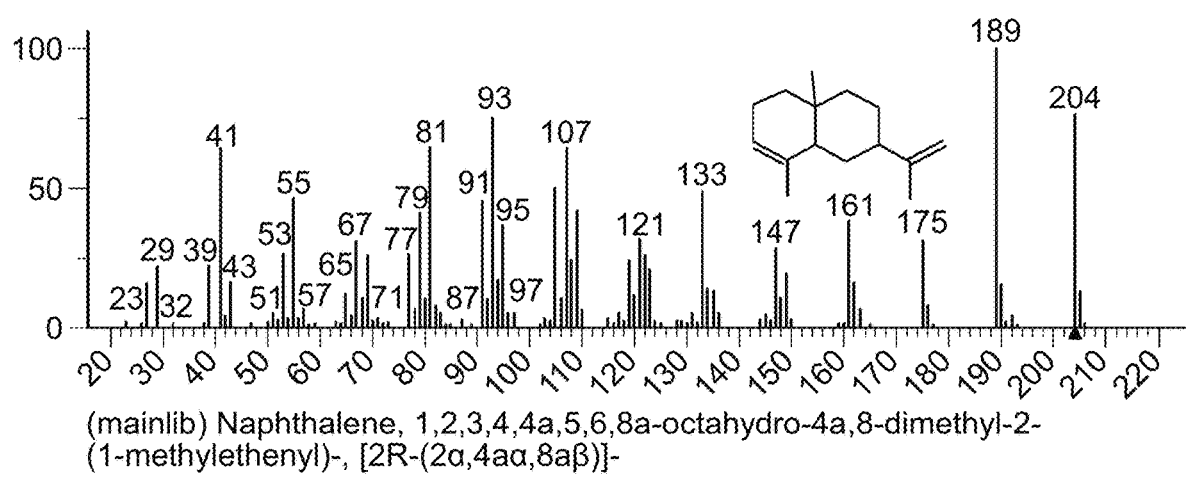
FIG. 2I. MS electron ionization fragmentation pattern for selinene, present in cultures of *Scedosporium apiospermum*.
Figure 2J:
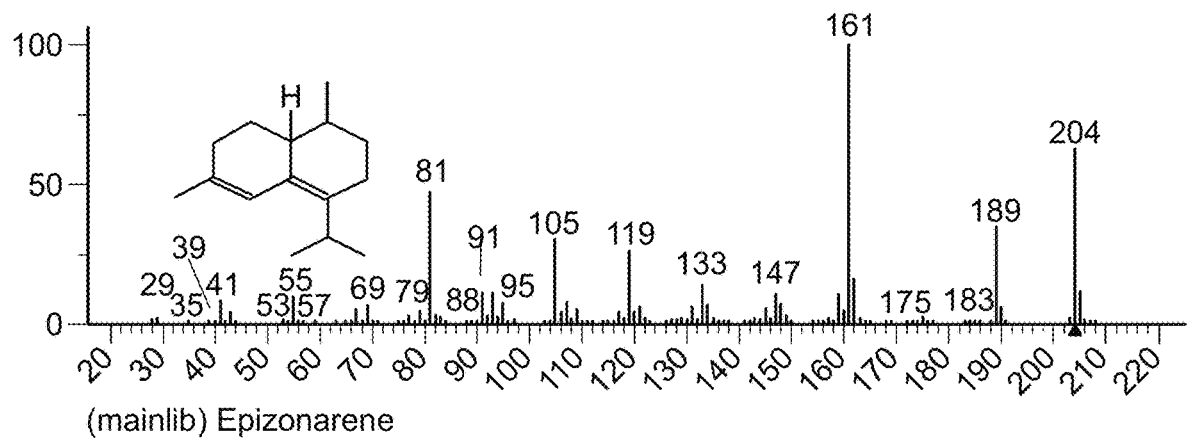
FIG. 2J. MS electron ionization fragmentation pattern for epizonarene, present in cultures of *Scedosporium apiospermum*.
Figure 2K:
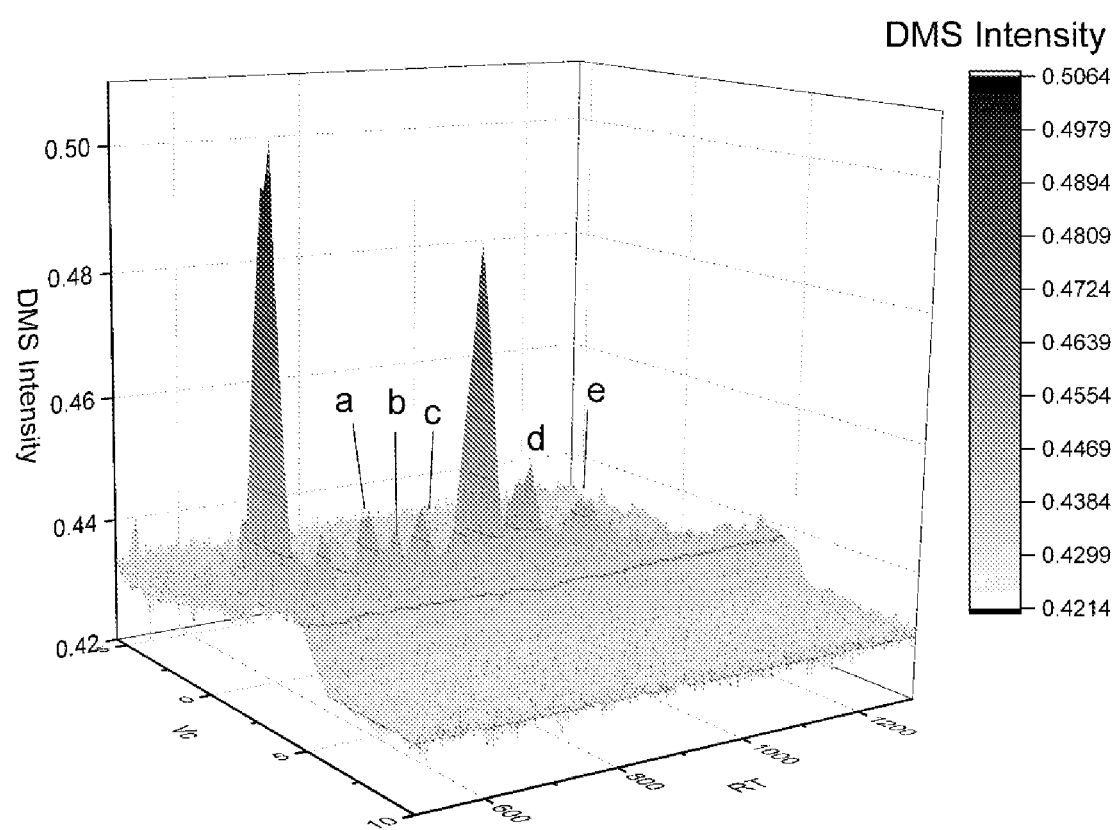
FIG. 2K. GC-differential mobility spectrometry spectra of *S. apiospermum:* (a) α-Gurjunene (Vc=4V, RT=621.92 s), (b) himachalene (Vc=4V, RT=661.8), (c) selina-5,11-diene (Vc=4V, RT=697.6 s), (d) γ-gurjunene (Vc=4.4V, RT=861.3 s), (e) selinene (Vc=4V, RT=951.3 s)
Figure 2L:
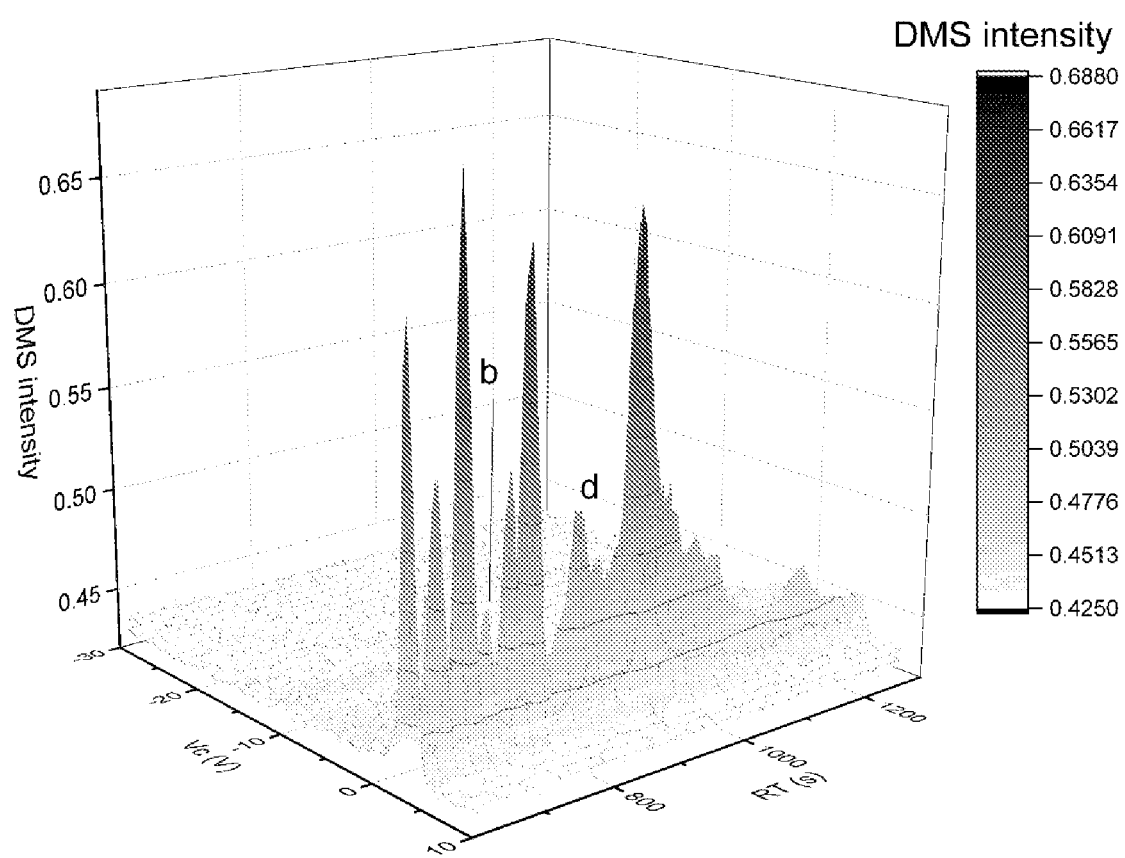
FIG. 2L. GC-differential mobility spectrometry spectra of *L. prolificans:* (b) himachalene, (d) γ-gurjunene FIG. 2M. GC-differential mobility spectrometry spectra of *S. boydii:* (d) γ-gurjunene (Vc=4V, RT=840 s)
Figure 2M:
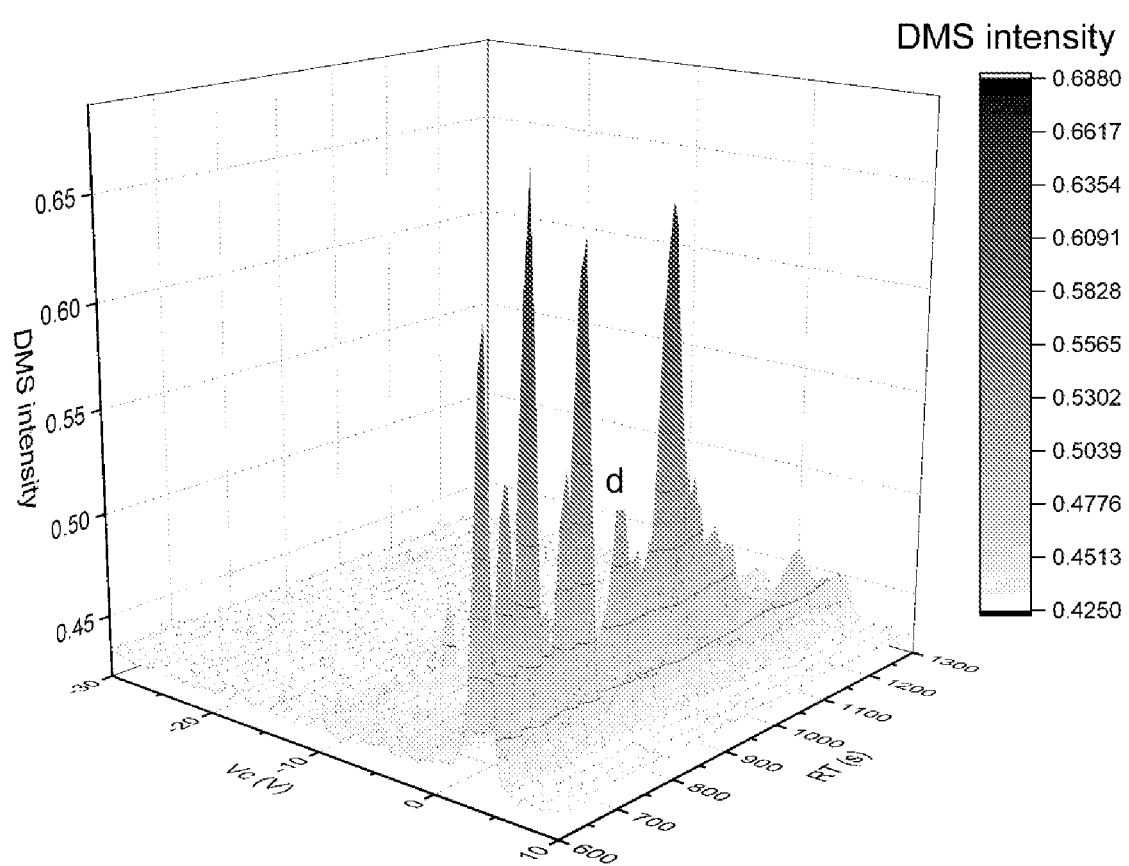
Figure 3A:
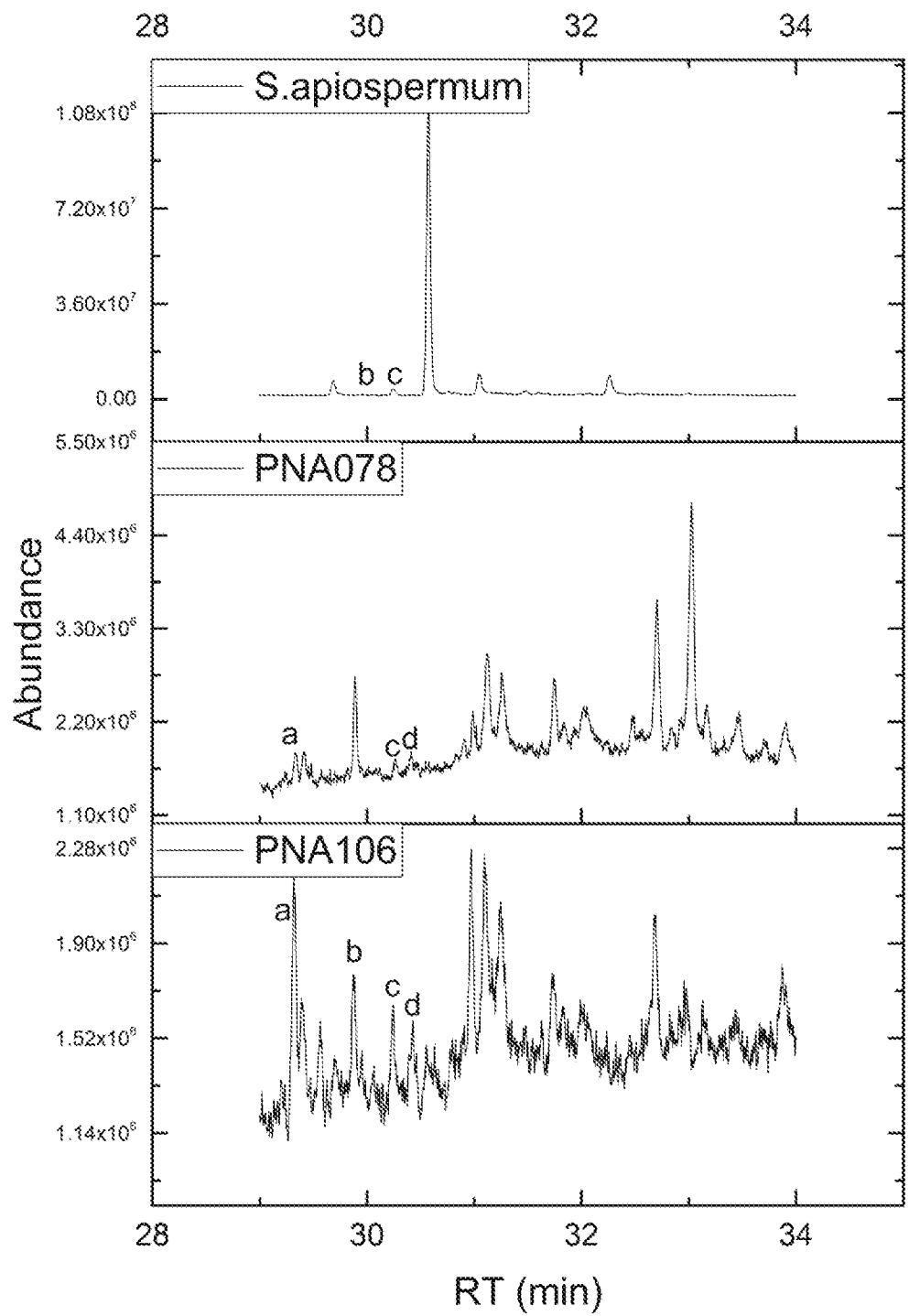
FIG. 3A. Secondary metabolite breath signature of 2 patients with *S. apiospermum* infections, aligned with an in vitro culture of *S. apiospermum*. Peaks are: (a) 1H-Indene, 2,3,3a,4-tetrahydro-3,3a,6-trimethyl-1-(1-methylethyl)-, (b) β-gurjunene, (c) β-longipinene, and (d) isocomene, with MS fragmentation patterns presented below (and for compounds identified in vitro, above); the last compound β-guaiene only became apparent with antifungal treatment in one of these patients.
Figure 3B:
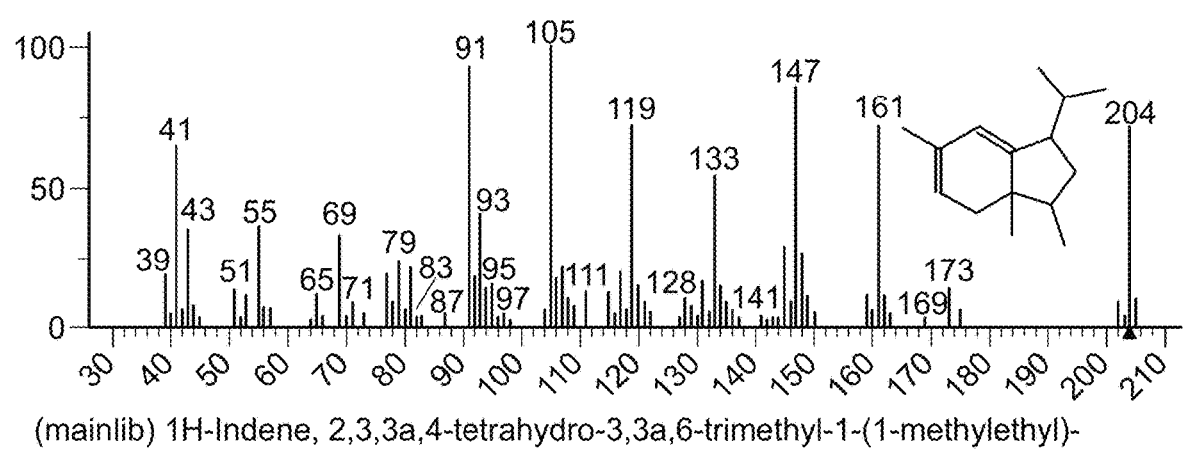
FIG. 3B. MS electron ionization fragmentation pattern for 1H-Indene, 2,3,3a,4-tetrahydro-3,3a,6-trimethyl-1-(1-methylethyl)-, present in the breath of 2 patients with disseminated *Scedosporium apiospermum* infection.
Figure 3C:
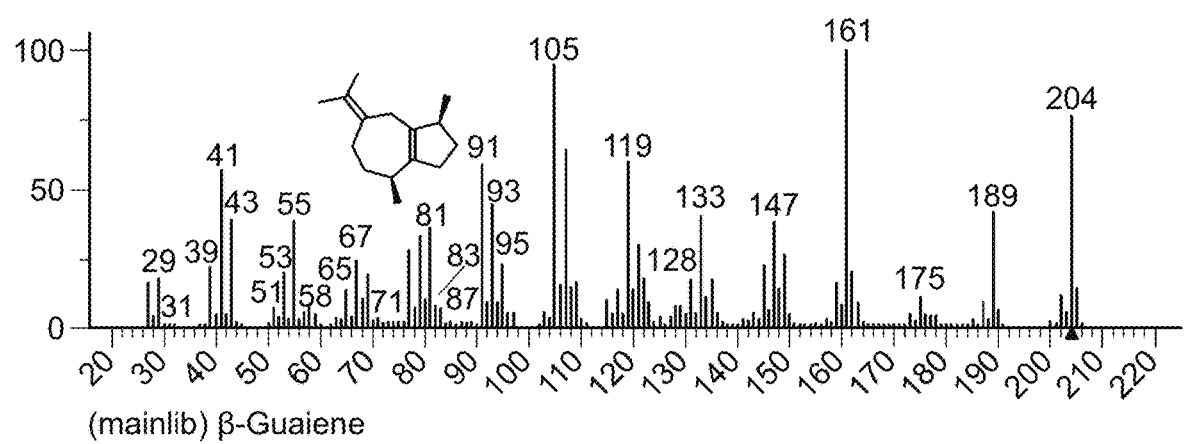
FIG. 3C. MS electron ionization fragmentation pattern for β-guaiene, present in the breath of 2 patients with disseminated *Scedosporium apiospermum* infection.

There were overlapping volatile metabolites and some species-specific metabolites in *Scedosporium* and *Lomentospora. Scedosporium apiospermum* produced a complex profile of: α-longipinene, β-longipinene, α-gurjunene, β-gurjunene, γ-gurjunene, isocomene, trans-α-bergamotene, himachalene, bisabolene, cadinene, selina-5,11-diene, aromandendrene, alloaromadendrene, naphthalene, 1,2,4a,5,6, 8a-hexahydro-4,7-dimethyl-1-(1-methylethyl)-, selinene, and epizonarene (FIGS. 1C, 1E, 1G, 1H, 1K, 1Q, 1S, 2B-J; 2K). *Lomentospora prolificans* emitted a profile of himachalene and γ-gurjunene (FIGS. 1H, 2D; 2L). *Scedosporium boydii* emitted γ-gurjunene (FIGS. 2D; 2M).

Figure 4A:
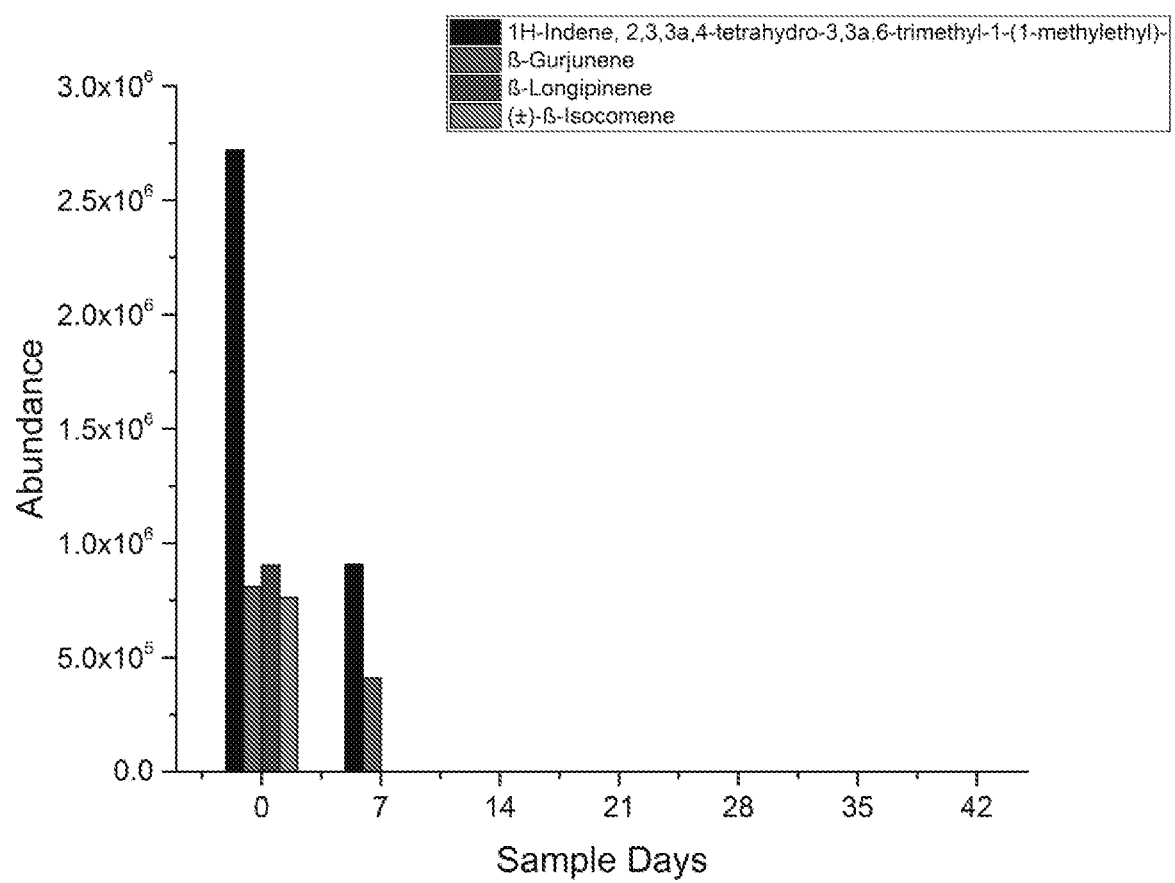
FIGS. 4A-B. Serial changes in breath volatile metabolite abundances in 2 patients with disseminated *S. apiospermum* infection with antifungal therapy.
Figure 4B:
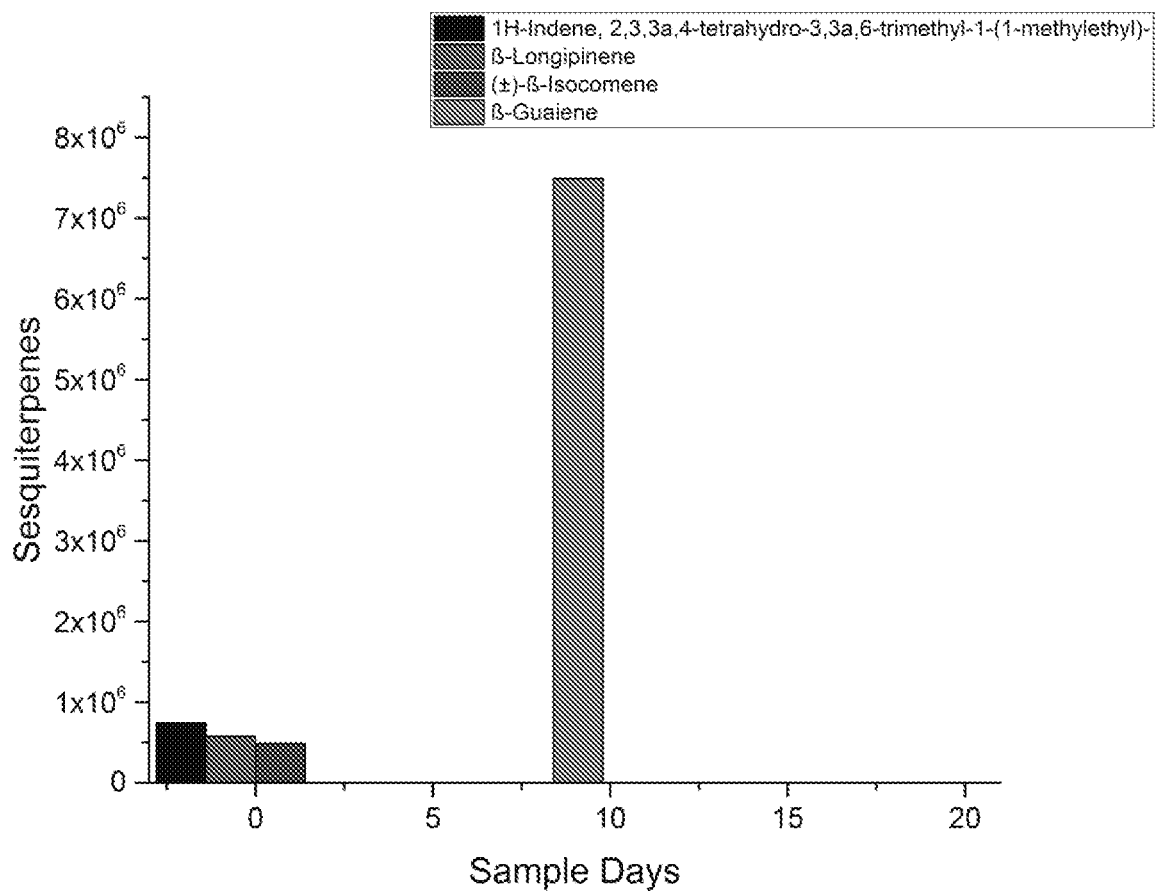
Figure 5A:
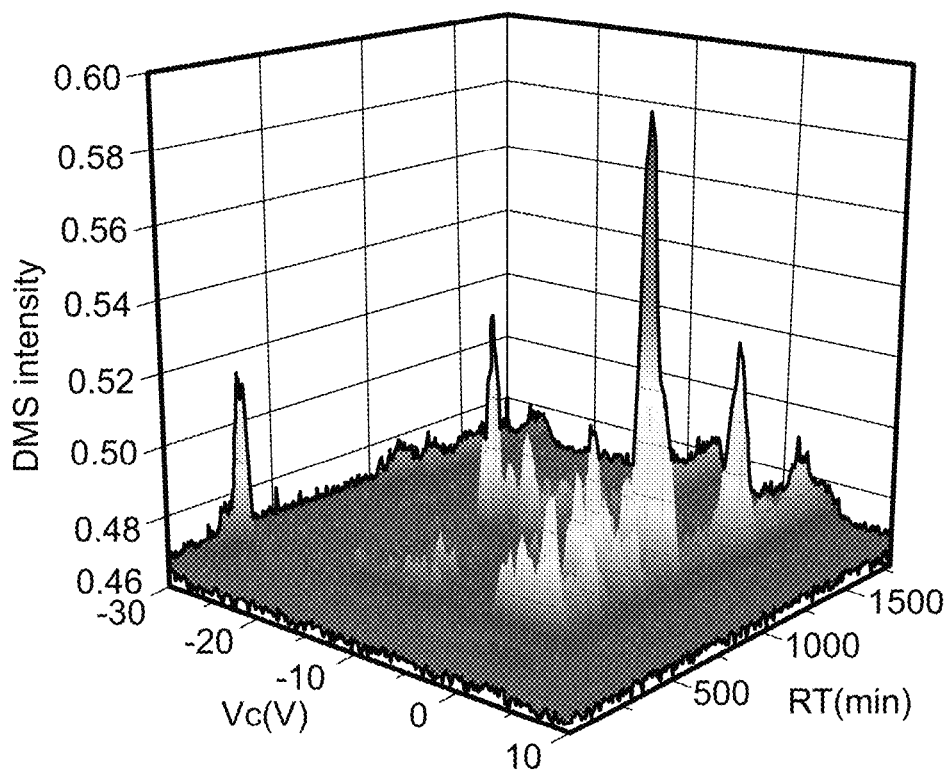
FIGS. 5A-B. GC-DMS plots of breath from a patient with invasive *S. apiospermum* infection at baseline (5A) and after antifungal therapy (5B)—plot of compensation voltage (Vc) vs. retention time (RT, in milliseconds) vs. DMS signal intensity.
Figure 5B:
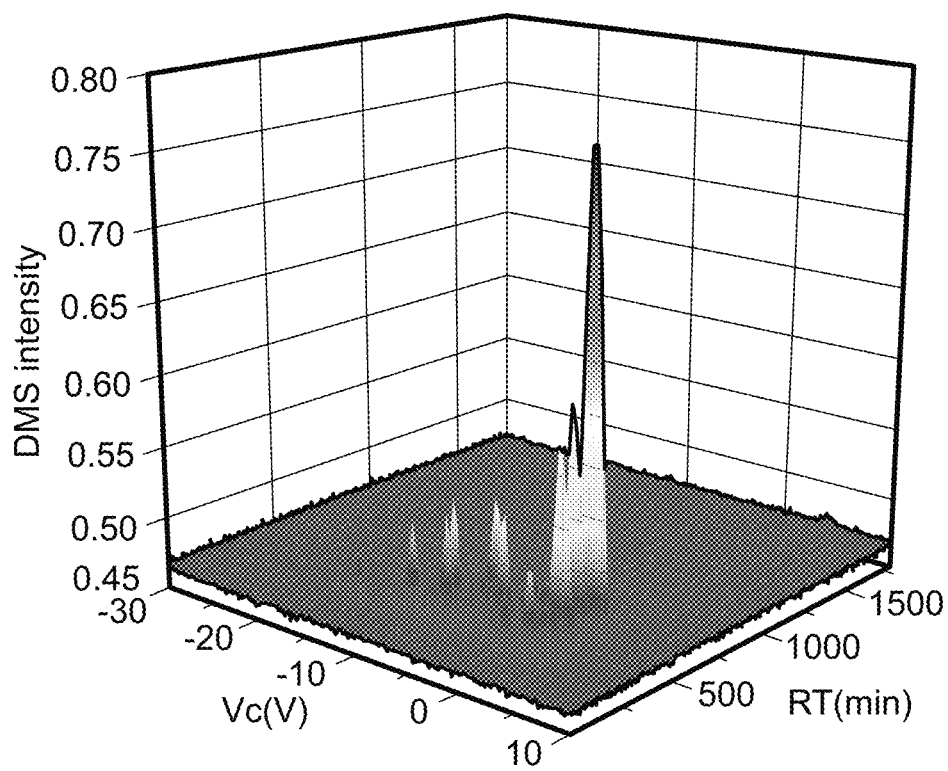

Patient breath samples: Two (of 2) patients with disseminated *S. apiospermum* infection (with growth of this organism from biopsy specimens of sterile sites) had a breath signature of 1H-Indene, 2,3,3a,4-tetrahydro-3,3a,6-trimethyl-1-(1-methylethyl)-, β-gurjunene, β-longipinene, isocomene, and β-guaiene (FIGS. 1C, 1E 2C, 3B-C). Three of these elements (β-gurjunene, β-longipinene, isocomene) were predicted by in vitro cultures of *S. apiospermum*, while 2 elements (1H-Indene, 2,3,3a,4-tetrahydro-3,3a,6-trimethyl-1-(1-methylethyl)-, β-guaiene) were only identified in the patient breath samples, with the overlay of the lung environment and the mold's interaction with the host's immune response. This breath signature disappeared over a period of 7-10 days in these two patients with antifungal therapy (FIGS. 4A-B); these compounds were also discernible on GC-DMS analysis of breath, disappearing with antifungal therapy (FIGS. 5A-B).

Conclusions: *Fusarium, Scedosporium*, and *Lomentospora* species produce a diverse array of volatile sesquiterpene secondary metabolites; some of these metabolites are produced by multiple species, while others appear to be species-specific. Breath samples from two patients with invasive *S. apiospermum* infection showed a signature of 1H-Indene, 2,3,3a,4-tetrahydro-3,3a,6-trimethyl-1-(1-methylethyl)-, β-gurjunene, β-longipinene, isocomene, and β-guaiene, with some overlap with in vitro cultures of *S. apiospermum*. These volatile secondary metabolite signatures are useful in the noninvasive, breath-based identification of patients with invasive fusariosis and scedosporiosis, the differentiation of these patients from those with invasive aspergillosis, other mycoses, and other infections, and the monitoring of response to antifungal therapy in patients with these infections.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for diagnosing and treating a subject with scedosporiosis, the method comprising:
   obtaining a sample comprising breath of a subject suspected of comprising *Scedosporium* species fungi isolated from the subject;
   detecting the presence of two, three, or more volatile organic compounds (VOCs) produced by the *Scedosporium* species in the sample comprising breath from the subject suspected of comprising *Scedosporium* isolated from the subject, wherein the VOCs are selected from the group consisting of (a) 1H-Indene, 2,3,3a,4-tetrahydro-3,3a,6-trimethyl-1-(1-methylethyl)-, (b) β-guaiene, (c) β-longipinene, (d) β-gurjunene, and (e) isocomene;
   diagnosing the subject as having scedosporiosis when there are two, three or more of the VOCs present in the sample; and
   administering an antifungal treatment to the subject diagnosed as having scedosporiosis.

2. The method of claim 1, wherein the treatment comprises administration of one or more doses of one or more antifungal compounds.

3. A method of treating a subject who is diagnosed as having an *Scedosporium apiospermum, S. prolificans*, or *S. boydii* infection, the method comprising:
   obtaining a sample comprising breath of a subject suspected of comprising *Scedosporium apiospermum, S. prolificans*, or *S. boydii* isolated from the subject; and:
   diagnosing the subject as having an *S. apiospermum* infection based on the presence of (a) 1H-Indene, 2,3,3a,4-tetrahydro-3,3a,6-trimethyl-1-(1-methylethyl)-, (b) β-guaiene, (c) (β-longipinene, (d) (β-gurjunene, and (e) isocomene in the sample ;
   diagnosing the subject as having an *S. prolificans* infection based on the presence of only himachalene and γ-gurjunene in the sample ; and
   diagnosing the subject as having an *S. boydii* infection based on the presence of only γ-gurjunene in the sample;
   and administering an antifungal treatment to the subject who is diagnosed as having the *Scedosporium apiospermum, S. prolificans*, or *S. boydii* infection.

4. The method of claim 1, further comprising:
   determining a first level of the two, three, or more VOCs produced by the *Scedosporium* species in the sample from the subject before administration of the antifungal treatment;
   determining a second level of the VOCs in a sample obtained after administration of the antifungal treatment to the subject; and
   comparing the first and second levels of VOCs, wherein a decrease in the VOCs indicates that the treatment has been effective in treating the scedosporiosis in the subject, and an increase or no change indicates that the treatment has not been effective in treating the scedosporiosis in the subject.

5. The method of claim 1, wherein determining the presence of a VOC comprises assaying the sample to detect the presence of the VOC.

6. The method of claim 5, wherein assaying the sample to detect the presence of the VOC comprises using a gas chromatography (GC) or spectrometry method.

7. The method of claim 6, wherein the spectrometry method is mobility spectrometry (IMS) or differential mobility spectrometry (DMS).

8. The method of claim 1, wherein the subject is a human.

9. The method of claim 5, wherein the subject is a human.

10. The method of claim 2, wherein the antifungal compound is an amphotericin B formulation or an azole antifungal compound.

* * * * *